United States Patent
Ott et al.

(10) Patent No.: US 10,876,081 B2
(45) Date of Patent: Dec. 29, 2020

(54) METHOD FOR THE PRODUCTION OF SCENT CAPSULES WITH IMPROVED SURFACTANT STABILITY

(71) Applicant: SYMRISE AG, Holzminden (DE)

(72) Inventors: Patrick Ott, Holzminden (DE); Daniela Gregor, Holzminden (DE); Kolja Behrens, Polle (DE); Wiebke Begemann, Höxter (DE)

(73) Assignee: Symrise AG, Holzminden (DE)

( * ) Notice: Subject to any disclaimer, the term of this patent is extended or adjusted under 35 U.S.C. 154(b) by 60 days.

(21) Appl. No.: 16/080,499

(22) PCT Filed: Feb. 29, 2016

(86) PCT No.: PCT/EP2016/054244
§ 371 (c)(1),
(2) Date: Aug. 28, 2018

(87) PCT Pub. No.: WO2017/148504
PCT Pub. Date: Sep. 8, 2017

(65) Prior Publication Data
US 2019/0062676 A1    Feb. 28, 2019

(51) Int. Cl.
| | |
|---|---|
| *C11D 3/50* | (2006.01) |
| *A61K 8/11* | (2006.01) |
| *A61K 8/33* | (2006.01) |
| *A61K 8/37* | (2006.01) |
| *A61Q 13/00* | (2006.01) |
| *B01J 13/02* | (2006.01) |
| *A61K 8/34* | (2006.01) |
| *A61K 8/81* | (2006.01) |

(52) U.S. Cl.
CPC ............... *C11D 3/505* (2013.01); *A61K 8/11* (2013.01); *A61K 8/33* (2013.01); *A61K 8/34* (2013.01); *A61K 8/37* (2013.01); *A61K 8/8129* (2013.01); *A61Q 13/00* (2013.01); *B01J 13/02* (2013.01)

(58) Field of Classification Search
None
See application file for complete search history.

(56) References Cited

U.S. PATENT DOCUMENTS

| | | | |
|---|---|---|---|
| 4,110,626 A | 8/1978 | Katada et al. | |
| 5,354,559 A | 10/1994 | Morehouse | |
| 2008/0176780 A1* | 7/2008 | Warr | A61K 8/0237 510/103 |
| 2011/0118161 A1* | 5/2011 | Looft | A01N 25/28 510/119 |
| 2017/0065993 A1* | 3/2017 | Burrowes | B05B 11/3047 |

FOREIGN PATENT DOCUMENTS

| | | |
|---|---|---|
| EP | 1064910 A1 | 1/2001 |
| WO | 2006/082536 A1 | 8/2006 |
| WO | 2014/095427 A1 | 6/2014 |

* cited by examiner

Primary Examiner — Jeffrey D Washville
(74) Attorney, Agent, or Firm — Dilworth & Barrese, LLP

(57) ABSTRACT

The invention relates to a method for producing scent capsules with improved surfactant stability, comprising the following steps: (a) providing a scent composition containing at least one scent which has at least one functional group that can form an acid group by means of oxidation or hydrolysis, and (b) encapsulating the scent mixture, characterised in that a scent composition is used that has an acid value of no more than 5 mg KOH/g immediately before encapsulation.

19 Claims, 1 Drawing Sheet

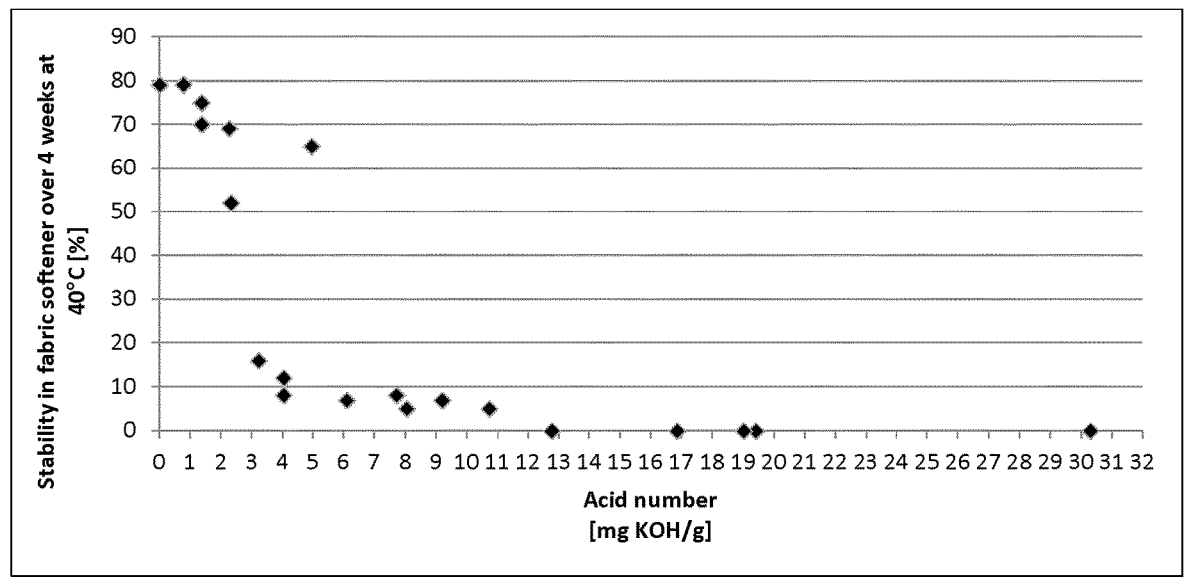

METHOD FOR THE PRODUCTION OF SCENT CAPSULES WITH IMPROVED SURFACTANT STABILITY

FIELD OF THE INVENTION

The invention pertains to the field of fragrances and concerns a method for producing encapsulated fragrances that show improved storage stability in an aqueous surfactant environment, capsules produced according to this method, agents comprising the capsules, and use of a special fragrance composition for the production of said capsules.

PRIOR ART

Fragrances are among the typical components of surfactant agents, such as e.g. shampoos, liquid detergents or laundry softeners. As a rule, this serves two purposes, specifically to provide the product with a pleasant fragrance on the one hand and to transfer this fragrance to the substrate as well—e.g. the skin, hair, or fabrics—on the other.

A trend has been observed in recent years of adding fragrances to formulations not directly, but in encapsulated form. There are two reasons for this as well: fragrances are often not chemically inert, i.e. they can react with other components of the formulation or are degraded by light or oxygen. It is therefore desirable to enclose them in an inert capsule so that further reactions are prevented and the fragrance content remains constant even in long-term storage or at higher temperatures. The capsules provide a second advantage, namely that if the capsule material is specifically selected so that it only allows the agents contained therein to diffuse out slowly ("controlled release"), or preferably, the shell does not break open until it is acted on by mechanical forces, release of the fragrance takes place either over a long period or not until the time of use. This effect is used in particular in the case of laundry softeners and liquid detergents: the washing process causes the capsules to adhere to the fibers of the laundry, and the fragrances are not released until the fabrics are worn.

However, it is problematic that the above-mentioned products typically contain large amounts of surfactant substances, and capsules are sometimes insufficiently stable in such an environment. A particular disadvantage observed by the applicant was that the insufficient stability cannot be attributed to the capsule material, but obviously has to do with the nature of the substances to be encapsulated.

The object of the present invention was therefore to provide fragrance capsules that show high storage stability in an aqueous surfactant environment, i.e. for example in a shampoo, a liquid detergent or a laundry softener, and therefore do not prematurely release the ingredients due to chemical degradation of the shell substance or diffusion through the capsule wall material.

DESCRIPTION OF THE INVENTION

A first subject matter of the invention concerns a method for producing fragrance capsules with improved surfactant stability, comprising the following steps:
(a) provision of a fragrance composition comprising at least one fragrance, which has at least one functional group that is capable by oxidation or hydrolysis of forming an acid group, and
(b) encapsulation of the fragrance mixture,
characterized in that a fragrance composition is used that has an acid number immediately prior to encapsulation of at most 5 mg KOH/g and preferably at most 3 mg KOH/g.

Surprisingly, it was found that the insufficient surfactant stability of the fragrance capsules is connected with the presence of aldehydic fragrances or fragrances with ester groups. In the presence of atmospheric oxygen, aldehydes show a tendency to form carboxylic acids, and esters (and accordingly lactones as well) can undergo saponification and thus also form carboxyl groups. The applicant has found that problem-free, storage-stable encapsulation is only possible with fragrance mixtures whose acid number does not exceed a maximum of 5 mg KOH/g, and preferably 3 mg KOH/g. If the fragrance mixtures have a higher acid number prior to encapsulation, the quality of the capsule wall will be severely impaired.

The technical teaching of the invention therefore lies in first testing the fragrance mixture prior to encapsulation with respect to the amount of free carboxylic acids. Here, determination of the acid number is preferably carried out according to DIN EN ISO 660:2009-10, wherein the acids are titrated with potassium hydroxide solution against phenolphthalein. The acid number then gives the amount in mg of potassium hydroxide required to neutralize the acids contained in 1 g of the sample.

As it is difficult to impossible to provide aldehydic fragrances containing no autoxidation products, the procedure in practice is to at least use freshly distilled products, or, on the other hand, mixtures of aldehydic and non-aldehydic fragrances that meet the acid number criterion. Alternatively, of course, one can dispense entirely with aldehyde fragrances (and at the same time, of course, fragrances having free carboxyl functional groups). In many cases, however, this is not possible because these very aldehydic fragrances are among the most important representatives of this substance class.

Aldehydic or Ester Fragrances

Aldehydic fragrances, which also include the corresponding acetals, as well as esters and lactones, can be subdivided into the following groups, specifically
(i) aliphatic aldehydes and their acetals,
(ii) cycloaliphatic aldehydes, and/or
(iii) aromatic or araliphatic aldehydes,
(iv) aliphatic, aromatic or araliphatic esters, and/or
(v) lactones.
As well as respective mixtures thereof as discussed below by way of example, specifically:

Aliphatic aldehydes and acetals thereof, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

Cycloaliphatic aldehydes, such as e.g. 2,4-dimethyl-3-cyclohexenecarbaldehyde; 2-methyl-4-(2,2,6-trimethylcyclohexen-1-yl)-2-butenal; 4-(4-hydroxy-4-methyl pentyl)-3-cyclohexenecarbaldehyde; 4-(4-methyl-3-penten-1-yl)-3-cyclohexenecarbaldehyde;

Aromatic and araliphatic aldehydes, such as e.g. benzaldehyde; phenylacetaldehyde; 3-phenylpropanal; hydratropic aldehyde; 4-methyl benzaldehyde; 4-methylphenyl acetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; α-butyl cinnamaldehyde; α-amyl cinnamaldehyde; α-hexyl cinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4- dimethoxybenzaldehyde; 2-methyl-3-(4-methoxyphenyl) propanal; 2-methyl-3-(4-methylenedioxyphenyl)propanal;

Aliphatic carboxylic acid esters, such as e.g. (E)- and (Z)-3-hexenyl formiate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

Esters of cyclic alcohols, such as e.g. 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate;

Esters of araliphatic alcohols and aliphatic carboxylic acids, such as e.g. benzyl acetate; benzyl propionate; benzyl isobutyrate; benzyl isovalerate; 2-phenethyl acetate; 2-phenethyl propionate; 2-phenethyl isobutyrate; 2-phenethyl isovalerate; 1-phenethyl acetate; α-trichlormethylbenzyl acetate; α,α-dimethylphenethyl acetate; α,α-dimethylphenethyl butyrate; cinnamyl acetate; 2-phenoxyethyl isobutyrate; 4-methoxybenzyl acetate;

Esters of cycloaliphatic carboxylic acids, such as e.g. allyl-3-cyclohexyl propionate; allylcyclohexyl oxyacetate; methyl dihydrojasmonate; methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

Aromatic and araliphatic carboxylic acid esters, such as e.g. methyl benzoate; ethyl benzoate; hexyl benzoate; benzyl benzoate; methylphenyl acetate; ethyl phenyl acetate; geranyl phenyl acetate; phenethyl phenylacetate; methyl cinnamate; ethyl cinnamate; benzyl cinnamate; phenethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenethyl salicylate; methyl-2,4-dihydroxy-3,6-dimethyl benzoate; ethyl-3-phenylglycidate; ethyl-3-methyl-3-phenylglycidate.

In Table A below, aldehydes, acetals, esters and lactones that are particularly preferred in the context of the method according to the invention as representatives of groups (i) through (v) are listed with their commercial names.

TABLE A

| Preferred fragrances | | |
|---|---|---|
| ALDEHYDES | ACETALS | ESTERS |
| 2-METHYLPENTANAL | FLOROPAL | JASMAL |
| ALDEHYD C12 MNA HM | HEPTANAL DIETHYL ACETAL | JESSEMAL |
| ALDEHYDE C 4 | NONADIENAL DIETHYL ACETAL | KHARISMAL |
| ALDEHYDE C 5 | OKOUMAL | TIRAMISONE ® |
| ALDEHYDE C 6 | PHENYLACET ALD. GLYCERIN ACETAL | |
| ALDEHYDE C 7 | PHENYLACETALDEHYDE DIMETHYLACETAL | |
| ALDEHYDE C 8 | | |
| ALDEHYDE C 9 | | |
| ALDEHYDE C10 | | |
| ALDEHYDE C11 ISO | | |
| ALDEHYDE C11 MOA PURE | | |
| ALDEHYDE C11 UNDECANAL | | |
| ALDEHYDE C11 UNDECYLENIC 10% DEP | | |
| ALDEHYDE C12 | | |
| ALDEHYDE C12 MNA | | |
| ALDEHYDE C13 | | |
| ALDEHYDE MANDARIN | | |
| AMYLCINNAMIC ALDEHYDE ALPHA | | |
| ANISALDEHYDE-O | | |
| ANISYL ALDEHYDE | | |
| BENZALDEHYDE NAT. | | |
| BERGAMAL | | |
| BORONAL | | |
| BOURGEONAL | | |
| CAMPHOLENIC ALDEHYDE | | |
| CANTHOXAL | | |
| CETONAL | | |
| CINNAMIC ALDEHYDE | | |
| CITRAL | | |
| CITRONELLAL HM | | |
| CITRONELLYL OXYACETALDEHYDE | | |
| CITRYLAL | | |
| CITRYLAL E HM | | |
| CORTEX ALDEHYDE | | |
| CORTEX ALDEHYDE 50 PCT PEOMOSA | | |
| CROTONIC ALDEHYDE | | |
| CUMIN ALDEHYDE | | |

TABLE A-continued

Preferred fragrances

| ALDEHYDES | ACETALS | ESTERS |
|---|---|---|
| CYCLAMEN ALDEHYDE | | |
| DECADIENAL TRANS,TRANS-2,4 | | |
| DECENAL CIS-4 | | |
| DECENAL TRANS-2 | | |
| DECENAL TRANS-2 NAT | | |
| DECENAL TRANS-4 | | |
| DECENAL-9,1 | | |
| DODECADIENAL 2,6 | | |
| DODECENAL TRANS-2 | | |
| DUPICAL | | |
| EPOXYDECENAL-4,5-2 10% TRI | | |
| ETHYLHEXANAL-2 | | |
| FARENAL ® | | |
| FLORHYDRAL | | |
| GERALDEHYDE | | |
| HELIONAL | | |
| HELIOPAN | | |
| HELIOTROPIN | | |
| HEPTADIENAL TRANS,TRANS-2,4 | | |
| HEPTENAL CIS-4 | | |
| HEPTENAL TRANS-2 | | |
| HEXENAL TRANS-2 | | |
| HEXYLCINNAMIC ALDEHYDE ALPHA | | |
| HYDRATROPIC ALDEHYDE | | |
| HYDROXYCITRONELLAL | | |
| INTRELEVEN ALDEHYDE SPEC. | | |
| ISONONYL ALDEHYDE | | |
| ISOVALERIC ALDEHYDE | | |
| LEMON ALDEHYDE H&R JS I | | |
| LILIAL | | |
| LIMONENAL | | |
| LINOLAL | | |
| LYRAL | | |
| MAJANTAL | | |
| MANDARINAL | | |
| MANDARIN ALDEHYDE 10% IN TEC BHT | | |
| MEFRANAL | | |
| MELONAL ® | | |
| METHOXYCITRONELLAL | | |
| METHYLBUTYRALDEHYDE | | |
| METHYLCINNAMIC ALDEHYDE ALPHA | | |
| METHYL PHENYLPENTENAL-4,2,2 | | |
| METHYL THIOPROPANAL-3 | | |
| METHYL TRIDECANAL-12 10% VT | | |
| METHYL-3-BUTEN-2-AL | | |
| METHYL-5-PHENYL-2-HEXEN-2-AL | | |
| MUGENAL 50 DPG | | |
| NEOCYCLOCITRAL | | |
| NONADIENAL TRANS,CIS-2,6 | | |
| NONENAL CIS-6 | | |
| NONENAL TRANS-2 | | |
| NORMAJANTAL | | |
| OCTENAL TRANS-2 | | |
| ONCIDAL ® 3/060251 | | |
| PENTENAL TRANS-2 | | |
| PERILLA ALDEHYDE | | |
| PHENYLACETALDEHYDE | | |
| PHENYLBUTENAL TRANS-2,2 | | |
| PHENYLPROPYL ALDEHYDE | | |
| PINOACETALDEHYDE | | |
| PROFARNESAL | | |
| PROPIONALDEHYDE 2-(P-TOLYL) | | |
| PROPIONIC ALDEHYDE | | |
| PS-IRALDEIN X NEW | | |
| SAFRANAL | | |
| SALICYLIC ALDEHYDE FG | | |
| SILVIAL | | |
| TETRAHYDROCITRAL | | |

TABLE A-continued

Preferred fragrances

| ALDEHYDES | ACETALS | ESTERS |
|---|---|---|
| TIGLIC ALDEHYDE-2,2 | | |
| TOLYL ALDEHYDE PARA FG | | |
| TRIDECENAL TRANS-2 | | |
| TRIFERNAL | | |
| UNDECADIENAL-2,4 | | |
| UNDECENAL TRANS-2 | | |
| VERATRALDEHYDE | | |
| VERNALDEHYDE | | |
| VERTOCITRAL | | |
| VERTOMUGAL | | |
| VERTOPRENAL | | |
| VERTRAL RAW | | |
| CINNAMALDEHYDE NAT. HM | | |

Further Fragrances

As explained above, fragrance compositions are preferably used that comprise at least one further fragrance comprising neither an aldehyde nor an acetal, ester or lactone functional group. Such compositions, in particular perfume oils, preferably comprise two, three, four, five, six, seven, eight, nine, or more fragrances or flavors, selected in particular from the substances mentioned below:

Extracts of natural raw materials, such as essential oils, concretes, absolutes, resins, resinoids, balsams, tinctures such as e.g. ambra tincture; amyris oil; angelica seed oil; angelica root; anis oil; valerian oil; basil oil; tree moss absolute; bay oil; mugwort oil; benzoin resin; bergamot oil; beeswax absolute; birch tar oil; bitter almond; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill oil; dill seed oil; eau de brouts absolute; oakmoss absolute; elemi oil; estragon oil; eucalyptus citriodora-oil; eucalyptus oil; fennel oil; pine needle oil; galbanum oil; galbanum resin; geranium oil; grapefruit oil; guaiac wood oil; gurjun balsam; gurjun balsam oil, helichrysum absolute; helichrysum oil; ginger oil; iris root absolute; iris root oil; jasmine absolute; calamus oil; camellia oil blue; camellia oil roman; carrot seed oil; cascarilla oil; pine needle oil; spearmint oil; cumin oil; labdanum oil; labdanum absolute; labdanum resin; lavandin absolute; lavandin oil; lavender absolute; lavender oil; lemon grass oil; lovage oil; lime oil distilled; lime oil pressed; linalool oil; litsea cubeba oil; laurel leaf oil; macis oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opoponax oil; orange blossom absolute; orange oil; oregano oil; palmarosa oil; patchouli oil; perilla oil; Peruvian balsam oil; parsley leaf oil; parsley seed oil; petitgrain oil; peppermint oil; pepper oil; allspice oil; pine oil; poley oil; rose absolute; rosewood oil; rose oil; rosemary oil; sage oil dalmatian; sage oil Spanish; sandalwood oil; celery seed oil; spike lavender oil; star anis oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; vermouth oil; wintergreen oil; ylang oil; ysop oil; civet absolute; cinnamon leaf oil; cinnamon bark oil; and fractions thereof or ingredients isolated therefrom;

Individual fragrances from one or more of the following groups:

Hydrocarbons, such as e.g. 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene;

Aliphatic alcohols, such as e.g. hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6, 6-tetramethyl-4-methyleneheptan-2-01; (E,Z)-2,6-nonadienol; 3,7-dimethyl-7-methoxyoctan-2-ol; 9-decenol; 10-undecenol; 4-methyl-3-decen-5-ol;

Aliphatic ketones and oximes thereof, such as e.g. 2-heptanone; 2-octanone; 3-octanone; 2-nonanone; 5-methyl-3-heptanone; 5-methyl-3-heptanonoxime; 2,4,4,7-tetramethyl-6-octen-3-on;

Aliphatic sulfur-containing compounds, such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

Aliphatic nitriles, such as e.g. 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

Acyclic terpene alcohols, such as e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5, 7-octatrien-3-ol; 2,6-dimethyl-2,5,7-octatrien-l-ol; and formates, acetates, propionates, isobutyrates, butyrates, isovalerates, pentanoates, hexanoates, crotonates, tiglinates, and 3-methyl-2-butenoates thereof;

Acyclic terpene aldehydes and ketones, such as e.g. geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, and 7-hydroxy-3,7-dimethyloctanal;

Cyclic terpene alcohols, such as e.g. menthol; isopulegol; α-terpineol; terpinenol-4; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerates, pentanoates, hexanoates, crotonates, tiglinates, and 3-methyl-2-butenoates;

Cyclic terpene aldehydes and ketones, such as e.g. menthone; isomenthone; 8-mer-captomenthan-3-one; carvone;

camphor; fenchone; α-ionone; β-ionone; α-n-methyl ionone; β-n-methyl ionone; α-isomethyl ionone; β-isomethyl ionone; α-irone; α-damascone; (α-damascone; β-damascenone; γ-damascone; δ-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; α-sinensal; β-sinensal; acetylated cedar wood oil (methyl cedryl ketone);

Cyclic alcohols, such as e.g. 4-tert-butylcyclohexanol; 3,3,5-trimethylcyclohexanol; 3-isocamphylcyclohexanol; 2,6,9-trimethyl-(Z2,Z5,E9)-cyclododecatrien-1-ol; 2-isobutyl-4-methyltetrahydro-2H-pyran-4-ol; from the group of the cycloaliphatic alcohols such as e.g. a,3,3-trimethyl-cyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers, such as e.g. cineol; cedryl methyl ether; cyclododecyl methyl ether; (ethoxymethoxy)cyclododecane; α-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; Rose oxide; 2-(2,4-dimethyl-3-cyclohexen-1-yl)-5-methyl-5-(1-methylpropyl)-1,3-dioxane;

Cyclic ketones, such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclo-penten-1-one; 3-methyl-cis-2-penten-1-yl-2-cyclo-penten-1-one; 3-methyl-2-pentyl-2-cyclopenten-1-one; 3-methyl-4-cyclopentadecenone; 3-methyl-5-cyclopentadecenone; 3-methyl-cyclopentadecanone; 4-(1-ethoxyvinyl)-3,3,5,5-tetramethylcyclohexanone; 4-tert-pentylcy-clohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

Cycloaliphatic ketones, such as e.g. 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert-butyl-(2,4-dimethyl-3-cyclohexen-1-yl)ketone;

Aromatic hydrocarbons, such as e.g. styrene and diphenylmethane;

Araliphatic alcohols, such as e.g. benzyl alcohol; 1-phenethyl alcohol; 2-phenethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Araliphatic ethers, such as e.g. 2-phenethyl methyl ether; 2-phenethyl isoamyl ether; 2-phenethyl-1-ethoxyethyl ether; phenyl acetaldehyde dimethyl acetal; phenyl acetaldehyde diethyl acetal; hydratropic aldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2]-m-dioxin;

Aromatic and araliphatic ketones, such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

Nitrogen-containing aromatic compounds, such as e.g. 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl-N-methyl anthranilate; Schiff bases of methyl anthranilate with 7-hydroxy-3,7-dimethyloctanal, 2-methyl-3-(4-tert-butylphenyl)propanal or 2,4-dimethyl-3-cyclohexene carbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine; 4-(4,8-dimethyl-3,7-nonadienyl)-pyridine;

Phenol, phenyl ethers and phenyl esters, such as e.g. estragole; anethole; eugenol; eugenyl menthol ether; isoeugenol; isoeugenyl methyl ether; thymol; carvacrol; diphenyl ether; (β-naphthyl methyl ether; β-naphthyl ethyl ether; β-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate; from the group of the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

Lactones, such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecandioate; ethylene-1,13-tridecandioate; coumarin; 2,3-dihydrocoumarin; octahydrocoumarin.

Fragrance Capsules

A further subject matter of the present invention concerns fragrance capsules that comprise the fragrance mixtures mentioned above with the acid number limitation or are produced using such mixtures.

The term capsules is understood to refer to spherical aggregates comprising at least one solid or liquid core that is enclosed by at least one continuous shell. Here, the fragrances can be in the form of macrocapsules with diameters of approximately 0.1 to approximately 5 mm or microcapsules with diameters of approximately 0.0001 to approximately 0.1 mm. The capsules can also have two or more shells of differing composition.

Encapsulation Materials

In this context, examples of suitable coating materials are starches, including their degradation products and chemically or physically produced derivatives (in particular dextrins and maltodextrins), gelatins, gum arabic, agar-agar, ghatti gum, gellan gum, modified and unmodified celluloses, pullulan, curdlan, carrageenans, alginic acid, alginates, pectin, inulin, xanthan gum and mixtures of two or more of these substances.

The solid encapsulation material is preferably a gelatin (in particular pork, beef, poultry, and/or fish gelatins), wherein this preferably has a swelling factor of greater than or equal to 20, more preferably greater than or equal to 24. Among these substances, gelatin is particularly preferred because it is readily available and can be obtained with different swelling factors.

Also preferred are maltodextrins (in particular based on grain, specifically corn, wheat, tapioca or potatoes), which preferably have DE values in the range of 10 to 20. Moreover, celluloses (e.g. cellulose ethers), alginates (e.g. sodium alginate), carrageenans (e.g. β-, ι-, λ- and/or κ-carrageenan), gum arabic, curdlan and/or agar-agar are also preferred.

Also preferred are alginate capsules, such as those explained in detail in the following documents: EP 0389700 A1, U.S. Pat. Nos. 4,251,195, 6,214,376, WO 2003 055587 or WO 2004 050069 A1.

In a further preferred embodiment, the shell of the capsules is composed of melamine-formaldehyde resins or coacervation products of cationic monomers or biopolymers (such as e.g. chitosan) and anionic monomers, such as e.g. (meth)acrylates or alginates. Also suitable as capsule materials are any desired synthetic, cationic and anionic polymers and their reaction products, as explained in further detail below.

Encapsulation Methods

The capsules are generally finely-dispersed liquid or solid phases enclosed by film-forming polymers, in the production of which the polymers are deposited on the material to be enclosed after emulsification and coacervation or interface polymerization. According to another method, molten waxes are absorbed by a matrix ("microsponge"), and these can also be enclosed as microparticles by film-forming polymers. According to a third method, particles are alternately coated with polyelectrolytes of different charges (the "layer-by-layer" method). The microscopically small capsules can be dried like powder. In addition to single-core microcapsules, multi-core aggregates, also referred to as microspheres, are also known that comprise two or more cores in a continuous shell material. Single or multi-core microcapsules can also be enclosed by an additional second, third, etc. shell. The shell can be composed of natural, semisynthetic or synthetic materials. Natural shell materials are for example gum arabic, agar-agar, agarose, maltodextrins, alginic acid or salts thereof, e.g. sodium or calcium alginate, fats and fatty acids, cetyl alcohol, collagen, chitosan, lecithins, gelatins, albumin, shellac, polysaccharides such as starch or dextran, polypeptides, protein hydrolysates, sucrose and waxes. Semisynthetic shell materials include chemically modified celluloses, in particular cellulose esters and ethers, e.g. cellulose acetate, ethyl cellulose, hydroxypropyl cellulose, hydroxypropyl methyl cellulose and carboxymethyl cellulose, and starch derivatives, in particular starch ethers and esters. Synthetic shell materials are for example polymers such as polyacrylates, polyamides, polyvinyl alcohol or polyvinyl pyrrolidone. Also suitable are aminoplasts, melamine-formaldehyde resins, polyureas, urea-formaldehyde resins and derivatives thereof.

Examples of microcapsules of the prior art are the following commercial products (the respective shell material is indicated in parentheses): Hallcrest Microcapsules (gelatin, gum arabic), Coletica Thalaspheres (maritime collagen), Lipotec Millicapsules (alginic acid, agar-agar), Induchem Unispheres (lactose, microcrystalline cellulose, hydroxypropyl methylcellulose); Unicerin C30 (lactose, microcrystalline cellulose, hydroxypropyl methylcellulose), Kobo glycospheres (modified starch, fatty acid esters, phospholipids), Softspheres (modified agar-agar) and Kuhs Probiol Nanospheres (phospholipids), and Primaspheres and Pri-masponges (chitosan, alginates) and Primasys (phospholipids).

Chitosan microcapsules and methods for their production are sufficiently well-known from the prior art [WO 01/01926, WO 01/01927, WO 01/01928, WO 01/01929]. Microcapsules with average diameters in the range of 0.0001 to 5, preferably 0.001 to 0.5 and in particular 0.005 to 0.1 mm, composed of a shell membrane and a matrix comprising the agents, can for example be obtained by
(a) preparing a matrix of gelling agents, cationic polymers and agents,
(b) optionally dispersing the matrix in an oil phase, and
(c) treating the dispersed matrix with aqueous solutions of anionic polymers, optionally removing the oil phase in the process.

Steps (a) and (c) can be interchanged by using anionic polymers instead of the cationic polymers in step (a) and vice versa.

The capsules can also be produced by alternately enclosing the agent with layers of polyelectrolytes having different charges (layer by layer technology). In this context, reference is made to the European Patent EP 1064088 B1 (Max Planck Society).

INDUSTRIAL APPLICABILITY

Further subject matter of the invention are surfactant agents contained in the capsules obtainable by the method according to the invention. In this context, these agents can on the one hand be cosmetic agents, and on the other detergents, rinsing agents and cleaning agents ("DRC agents"), which can be contained in the capsules in amounts of approximately 0.01 to approximately 10 wt %, preferably approximately 0.5 to 5 wt % and in particular approximately 0.8 to 1 wt %, based on the agents.

Cosmetic Agents

The cosmetic agents according to the invention, in particular personal care products, can further comprise typical excipients and additives, such as e.g. mild surfactants, oil components, emulsifiers, pearlizing waxes, bodying agents, thickeners, superfatting agents, stabilizers, polymers, silicone compounds, fats, waxes, lecithins, phospholipids, UV light protection factors, humectants, biogenic agents, antioxidants, deodorants, antiperspirants, anti-dandruff agents, film-forming agents, swelling agents, insect repellents, self-tanning agents, tyrosine inhibitors (depigmenting agents), hydrotropes, solubilizers, preservatives, perfume oils, dyes and the like.

Surfactants

As surfactant substances, anionic, nonionic, cationic and/or amphoteric or zwitterionic surfactants can be contained in the capsules, with the amount of these agents ordinarily being approximately 1 to 70, preferably 5 to 50 and in particular 10 to 30 wt %. Typical examples of anionic surfactants are soaps, alkylbenzene sulfonates, alkane sulfonates, olefin sulfonates, alkyl ether sulfonates, glyceryl ether sulfonates, α-methyl ester sulfonates, sulfofatty acids, alkyl sulfates, alkyl ether sulfates, glyceryl ether sulfates, fatty acid ether sulfates, hydroxy mixed ether sulfates, monoglyceride (ether) sulfates, fatty acid amide (ether) sulfates, mono- and dialkylsulfosuccinates, mono- and dialkylsulfosuccinamates, sulfotriglycerides, amide soaps, ether carboxylic acids and salts thereof, fatty acid isethionates, fatty acid sarcosinates, fatty acid taurides, N-acylamino acids, such as e.g. acyl lactylates, acyl tartrates, acyl glutamates and acyl aspartates, alkyl oligoglycoside sulfates, protein fatty acid condensates (in particular wheat-based plant products) and alkyl(ether) phosphates. If the anionic surfactants comprise polyglycol ether chains, these can have a conventional, but preferably a narrow homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed eithers or mixed formals, optionally partially oxidized alk(en)yl oligoglycosides or glucuronic acid derivatives, fatty acid-N-alkyl glucamides, protein hydrolysates (in particular wheat-based plant products), polyol fatty acid esters, sucrose esters, sorbitan esters, polysorbates and aminoxides. If the nonionic surfactants comprise polyglycol ether chains, these can have a conventional, but preferably a narrow homolog distribution. Typical examples of cationic surfactants are quaternary ammonium compounds, such as e.g. dimethyl distearyl ammonium chloride, and esterquats, in particular quaternized fatty acid trialkanolamine ester salts. Typical examples of amphoteric or zwitterionic surfactants are alkyl betaine, alkyl amidobetaines, aminopropionates, aminoglycinates, imidazolinium betaines and sulfobetaines. The above-mentioned surfactants are exclusively known compounds. Typical examples of particularly suitable mild, i.e. particularly skin-compatible surfactants are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, α-olefin sulfonates, ether carboxylic acids, alkyl oligoglycosides, fatty acid glucamides, alkyl amido betaines, amphoacetals and/or protein fatty acid condensates, the latter preferably based on wheat proteins.

Oil Components

Examples of suitable oil components include Guerbet alcohols based on fatty alcohols with 6 to 18, preferably 8 to 10 carbon atoms, esters of linear $C_6$-$C_{22}$ fatty acids with linear or branched $C_6$-$C_{22}$ fatty alcohols or esters of branched $C_6$-$C_{13}$-carboxylic acids with linear or branched $C_6$-$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, in particular 2-ethyl hexanol, esters of $C_{18}$-$C_{38}$-alkyl hydroxycarboxylic acids with linear or branched $C_6$-$C_{22}$ fatty alcohols, in particular dioctyl malate, esters of linear and/or branched fatty acids with polyhydric alcohols (such as e.g. propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty acids and/or Guerbet alcohols with aromatic carboxylic acids, in particular benzoic acid, esters of $C_2$-$C_{12}$-dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as e.g. dicaprylyl carbonate (Cetiol® CC), Guerbet carbonates based on fatty alcohols with 6 to 18, preferably 8 to 10 C atoms, esters of benzoic acid with linear and/or branched $C_6$-$C_{22}$ alcohols (e.g. Finsolv® TN), linear or branched, symmetrical or asymmetrical dialkyl ethers with 6 to 22 carbon atoms per alkyl group, such as e.g. dicaprylyl ether (Cetiol® OE), ring-opening products of epoxidized fatty acid esters with polyols, silicone oils (of the cyclomethicone or silicone methicone type, etc.) and/or aliphatic or naphthenic hydrocarbons, such as e.g. squalane, squalenes or dialkyl cyclohexanes.

Emulsifiers

Examples of suitable emulsifiers include nonionogenic surfactants from at least one of the following groups:

addition products of 2 to 30 mol of ethylene oxide and/or 0 to 5 mol of propylene oxide to linear fatty alcohols with 8 to 22 C atoms, fatty acids with 12 to 22 C atoms, alkylphenols with 8 to 15 C atoms in the alkyl group and alkylamines with 8 to 22 carbon atoms in the alkyl radical;

alkyl and/or alkenyl oligoglycosides with 8 to 22 carbon atoms in the alk(en)yl radical and ethoxylated analogs thereof;

addition products of 1 to 15 mol of ethylene oxide to castor oil and/or hardened castor oil;

addition products of 15 to 60 mol of ethylene oxide to castor oil and/or hardened castor oil;

partial esters of glycerol and/or sorbitan with unsaturated, linear or saturated, branched fatty acids with 12 to 22 carbon atoms and/or hydroxycarboxylic acids with 3 to 18 carbon atoms and adducts thereof with 1 to 30 mol of ethylene oxide;

partial esters of polyglycerol (average degree of autocondensation 2 to 8), polyethylene glycol (molecular weight 400 to 5000 g/mol), trimethylolpropane, pentaerythritol, sugar alcohols (e.g. sorbitol), alkyl glycosides (e.g. methyl glycoside, butyl glycoside, lauryl glycoside) and polyglycosides (e.g. cellulose) with saturated and/or unsaturated, linear or branched fatty acids with 12 to 22 carbon atoms and/or hydroxycarboxylic acids with 3 to 18 carbon atoms and adducts thereof with 1 to 30 mol of ethylene oxide;

mixed esters of pentaerythritol, fatty acids, citric acid and fatty alcohol and/or mixed esters of fatty acids with 6 to 22 carbon atoms, methylglucose and polyols, preferably glycerol or polyglycerol.

mono, di- and trialkyl phosphate and mono, di- and/or tri-PEG alkyl phosphate and salts thereof;

lanolin alcohols;

polysiloxane-polyalkyl-polyether copolymers or corresponding derivatives;

block copolymers, e.g. PEG-30 dipolyhydroxy stearate;

polymer emulsifiers, e.g. of the Pemulen type (TR-1,TR-2) from Goodrich or Cosmedia® SP from Cognis;

polyalkylene glycols and glycerol carbonate.

In the following, particularly suitable emulsifiers are discussed in further detail:

Alkoxylates. The addition products of ethylene oxide and/or propylene oxide to fatty alcohols, fatty acids, alkylphenols or castor oil constitute known, commercially obtainable products. These are homolog mixtures whose average degree of alkoxylation corresponds to the ratio of the amount of substance of ethylene oxide and/or propylene oxide to the substrates with which the addition reaction is carried out. $C_{12/18}$ fatty acid mono- and -diesters of addition products of ethylene oxide to glycerol are known as refatting agents for cosmetic preparations.

Alkyl and/or alkenyl oligoglycosides. Alkyl and/or alkenyl oligoglycosides and the production and use thereof are known from the prior art. In particular, they are produced by reacting glucose or oligosaccharides with primary alcohols with 8 to 18 carbon atoms. With respect to the glycoside radical, both monoglycosides in which a cyclic sugar radical is glycosidically bound to the fatty alcohol and oligomeric glycosides with a preferred degree of oligomerization of approximately 8 are suitable. Here, the degree of oligomerization is a statistical mean value on which a homologous distribution that is common for such technical products is based.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof, which may also secondarily comprise small amounts of triglyceride from the production process. Also suitable are addition products of 1 to 30, preferably 5 to 10 mol of ethylene oxide to the above-mentioned partial glycerides.

Sorbitan esters. Suitable sorbitan esters include sorbitan mono isostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Also suitable are addition products of 1 to 30, preferably 5 to 10 mol of ethylene oxide to the above-mentioned sorbitan esters.

Polyglycerol esters. Typical examples of suitable polyglycerol esters are polyglyceryl-2 dipolyhydroxystearate (Dehymuls® PGPH), polyglycerol-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, as well as mixtures thereof. Examples of further suitable polyol esters are mono, di- and triesters of trimethylol propane or pentaerythritol, optionally reacted with 1 to 30 mol of ethylene oxide, with lauric acid, coconut fatty acid, tallow fatty acid, palmitic acid, stearic acid, oleic acid, behenic acid and the like.

Anionic emulsifiers. Typical anionic emulsifiers are aliphatic fatty acids with 12 to 22 carbon atoms, such as e.g. palmitic acid, stearic acid or behenic acid, and dicarboxylic acids with 12 to 22 carbon atoms, such as e.g. azelaic acid or sebacic acid.

Amphoteric and cationic emulsifiers. Moreover, zwitterionic surfactants may be used as emulsifiers. Surfactant compounds having in the molecule at least one quaternary ammonium group and at least one carboxylate and one sulfonate group are referred to as zwitterionic surfactants. Particularly suitable zwitterionic surfactants are the so-called betaines, such as the N-alkyl-N,N-dimethyl ammonium glycinates, e.g. coconut alkyldimethyl ammonium glycinate, the N-acylaminopropyl-N,N-dimethyl ammonium glycinates, for example coconut acylaminopropyl dimethyl ammonium glycinate, 2-alkyl-3-carboxylmethyl-3-hydroxyethylimidazolines with 8 to 18 C atoms respectively in the alkyl or acyl group, and coconut acylaminoethyl hydroxyethyl carboxymethyl glycinate. Particularly preferred is the fatty acid amide derivative known by the CTFA name cocamidopropyl betaine. Further suitable emulsifiers are ampholytic surfactants. Ampholytic surfactants are understood to refer to surfactant compounds which, in addition to one $C_{8/18}$ alkyl or acyl group in the molecule, comprise at least one free amino group and at least one —COOH— or —$SO_3H$ group and are capable of forming inner salts. Examples of suitable ampholytic surfactants are N-alkylglycines, N-al-kylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with approximately 8 to 18 C atoms respectively in the alkyl group. Particularly preferred ampholytic surfactants are N-coconut alkylaminopropionate, coconut acylaminoethyl aminopropionate and $C_{12/18}$ acylsarcosine. Finally, cationic surfactants are also suitable as emulsifiers, wherein those of the esterquat type, preferably methyl quaternized difatty acid triethanolamine ester salts, are particularly preferred.

Fats and Waxes

Typical examples of fats are glycerides, i.e. solid or liquid plant or animal products that are essentially composed of mixed glycerol esters of higher fatty acids; examples of suitable waxes include natural waxes, such as e.g. candelilla wax, carnauba wax, Japan wax, esparto wax, cork wax, guaruma wax, rice-seed oil wax, sugarcane wax, ouricury wax, montan wax, beeswax, shellac wax, spermaceti, lanolin (wool wax), rump fat, ceresin, ozocerite (solid paraffin), petrolatum, paraffin waxes, microwaxes; chemically modified waxes (hard waxes), such as e.g. montan ester waxes, sasol waxes, hydrogenated jojoba waxes and synthetic waxes, such as e.g. polyalkylene waxes and polyethylene glycol waxes. In addition to fats, suitable additives also include fatlike substances, such as lecithins and phospholipids. The term lecithins is understood by the person having ordinary skill in the art to refer to glycerophospholipids formed from fatty acids, glycerol, phosphoric acid and choline by esterification. For this reason, lecithins are often referred to in the professional world as phosphatidyl cholines (PC). As examples of natural lecithins, the cephalins can be mentioned, which are also referred to as phosphatidic acids and constitute derivatives of 1,2-diacyl-sn-glycerol-3-phosphoric acids. In contrast, phospholipids are ordinarily understood to be mono- and preferably diesters of phosphoric acid with glycerol (glycerol phosphate), which are generally considered to be fats. In addition, sphingosines or sphingolipids are also suitable.

Pearlizing Waxes

Examples of suitable pearlizing waxes include alkylene glycol esters, specifically ethylene glycol distearate; fatty acid alkanolamides, specifically coconut fatty acid diethanolamide; partial glycerides, specifically stearic acid monoglyceride; esters of polyhydric, optionally hydroxy-substituted carboxylic acids with fatty alcohols with 6 to 22 carbon atoms, specifically long-chain esters of tartaric acid; fatty substances, such as e.g. fatty alcohols, fatty ketones, fatty aldehydes, fatty ethers and fatty carbonates having a total of at least 24 carbon atoms, specifically laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups and mixtures thereof.

Coolants

Coolants are compounds that produce a feeling of coolness on the skin. As a rule, these are menthol compounds, which—in addition to the parent substance menthol itself—are selected for example from the group composed of menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomenthyl glutamate (FEMA GRAS 4006), menthoxy-1,2-propanediol (FEMA GRAS 3784), methoxy-2-methyl-1,2-propanediol (FEMA GRAS 3849), and the methane carboxylic acid esters and amides WS-3, WS-4, WS-5, WS-12, WS-14 and WS-30 and mixtures thereof.

[1]FEMA stands for "Flavor and Extracts Manufacturers Association," and GRAS stands for "Generally Regarded As Safe." An FEMA GRAS designation means that the substance characterized in this manner has been tested according to standardized methods and is considered to be toxicologically safe.

A first important representative of these substances is monomethyl succinate (FEMA GRAS 3810). Both the succinate and the analogous monomethyl glutarate (FEMA GRAS 4006) are important representatives of monomethyl esters based on di- and polycarboxylic acids:

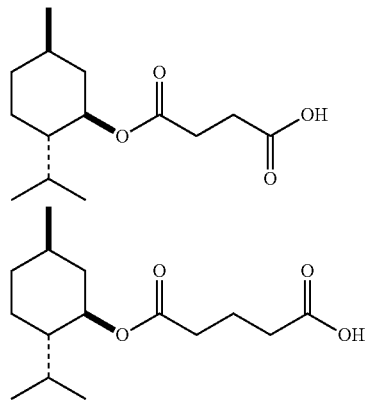

Examples of applications of these substances can be found for example in the documents WO 2003 043431 (Unilever) or EP 1332772 A1 (IFF).

The next important group of menthol compounds preferred in the context of the invention comprises carbonate esters of menthol and polyols, such as e.g. glycols, glycerol or carbohydrates, such as e.g. menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Also preferred are the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is sold under the name Frescolat® MGA. Among these substances, menthone glyceryl acetal/ketal, menthyl lactate and menthol ethylene glycol carbonate or menthol propylene glycol carbonate have proven to be most particularly advantageous, and these are sold by the applicant under the brand names Frescolat® MGA, Frescolat® ML, Frescolat® MGC and Frescolat® MPC.

Menthol compounds having a C—C bond at the 3 position, of which a number of representatives can also be used, were first developed in the 1970s. These substances are generally referred to as WS types. The parent substance is a menthol derivative in which the hydroxyl group is replaced by a carboxyl group (WS-1). All further WS types can be derived from this structure, such as e.g. the preferred species WS-3, WS-4, WS-5, WS-12, WS-14 and WS-30.

Bodying Agents and Thickeners

Primarily suitable as bodying agents are fatty alcohols or hydroxy fatty alcohols with 12 to 22 and preferably 16 to 18 carbon atoms, as well as partial glycerides, fatty acids or hydroxy fatty acids. Preferred is a combination of these substances with alkyl oligoglycosides and/or fatty acid N-methyl glucamides of the same chain length and/or polyglycerol poly-12-hydroxy stearates. Suitable thickeners are for example Aerosil grades (hydrophilic silicic acids), polysaccharides, in particular xanthan gum, guar-guar, agar-agar, alginates and tyloses, carboxymethylcellulose and hydroxyethyl- and hydroxypropylcellulose, furthermore higher molecular weight polyethylene glycol mono- and -diesters of fatty acids, polyacrylates (e.g. Carbopole® and Pemulen grades from Goodrich; Synthalene® from Sigma; Keltrol grades from Kelco; Sepigel grades from Seppic; Salcare grades from Allied Colloids), polyacrylamides, polymers, polyvinyl alcohol and polyvinyl pyrrolidone. Bentonites such as e.g. Bentone® Gel VS-5PC (Rheox), have also been found to be particularly effective, the latter being a mixture of cyclopentasiloxane, disteardimonium hectorite and propylene carbonate. Also suitable are surfactants, such as e.g. ethoxylated fatty acid glycerides, esters of fatty acids with polyols such as e.g. pentaerythritol or trimethylolpropane, fatty alcohol ethoxylates with a narrow homolog distribution, or alkyl oligoglycosides and electrolytes such as sodium chloride and ammonium chloride.

Superfatting Agents and Stabilizers

Superfatting agents suitable for use are substances such as e.g. lanolin and lecithin and polyethoxylated or acylated lanolin and lecithin derivatives, polyol fatty acid esters, monoglycerides and fatty acid alkanolamides, wherein the latter also serve as foam stabilizers.

Metal salts of fatty acids, such as e.g. magnesium, aluminum and/or zinc stearate or ricinolate, may be used as stabilizers.

Polymers

Suitable cationic polymers are for example cationic cellulose derivatives, such as e.g. a quaternized hydroxyethylcellulose that can be obtained under the name Polymer JR 400® from Amerchol, cationic starches, copolymers of diallyl ammonium salts and acrylamides, quaternized vinylpyrrolidone/vinylimidazole polymers such as e.g. Luviquat® (BASF), condensation products of polyglycols and amines, quaternized collagen polypeptides, such as e.g. lauryldimonium hydroxypropyl hydrolyzed collagen (Lamequat® L/Grünau), quaternized wheat polypeptides, polyethyleneimine, cationic silicone polymers, such as e.g. amodimethicone, copolymers of adipic acid and dimethylamino hydroxypropyl diethylenetriamine (Cartaretine®/Sandoz), copolymers of acrylic acid with dimethyl-diallyl ammonium chloride (Merquat® 550/Chemviron), polyaminopolyamides and crosslinked water-soluble polymers thereof, cationic chitin derivatives such as e.g. quaternized chitosan, optionally in the form of a microcrystalline dispersion, condensation products of dihaloalkylenes such as e.g. dibromobutane with bis-dialkylamines, such as e.g. bis-dimethylamino-1,3-propane, cationic guar gum, such as e.g. Jaguar® CBS, Jaguar® C-17, Jaguar® C-16 from Celanese, and quaternized ammonium salt polymers, such as e.g. Mirapol® A-15, Mirapol® AD-1, Mirapol® AZ-1 from Miranol.

Examples of suitable anionic, zwitterionic, amphoteric and nonionic polymers include for example vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and those crosslinked with polyols, acrylamidopropyl trimethylammonium chloride/acrylate copolymers, octylacrylamide/methyl methacrylate/tert-butylaminoethylmethacrylate/2-hydroxypropylmethacrylate copolymers, polyvinylpyrrolidone, vinylpyrrolidone/vinyl acetate copolymers, vinylpyrrolidone/dimethylaminoethylmethacrylate/vinylcaprolactam terpolymers and optionally derivatized cellulose ethers and silicones.

Silicone Compounds

Examples of suitable silicone compounds include dimethyl polysiloxanes, methyl phenyl polysiloxanes, cyclic silicones and amino, fatty acid, alcohol, polyether, epoxy, fluorine, glycoside and/or alkyl-modified silicone compounds, which can be either liquid or resinous at room temperature. Also suitable are simethicones that are mixtures of dimethicones having an average chain length of 200 to 300 dimethyl siloxane units and hydrogenated silicates.

UV Light Protection Factors

The term UV light protection factors is understood for example to refer to organic substances that are liquid or crystalline at room temperature (light protection filters), which are capable of absorbing ultraviolet rays and giving off the absorbed energy in the form of longer-wavelength radiation, e.g. heat. The UV light protection factors are ordinarily present in amounts of 0.1 to 5 and preferably 0.2 to 1 wt %. UVB filters can be oil-soluble or water-soluble. Examples of oil-soluble substances include, for example:

3-benzylidene camphor or 3-benzylidene norcamphor and derivatives thereof, e.g. 3-(4-methylbenzylidene) camphor;

4-aminobenzoic acid derivatives, preferably 4-(dimethylamino)benzoic acid-2-ethyl-hexyl ester, 4-(dimethylamino)benzoic acid-2-octyl ester and 4-(dimethylamino)benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, and 2-cyano-3,3-phenylcinnamic acid-2-ethylhexyl ester (octrylene);

esters of salicylic acid, preferably salicylic acid-2-ethylhexyl ester, salicylic acid-4-iso-propylbenzyl ester, and salicylic acid homomenthyl ester;

derivatives of benzophenone, preferably 2-hydroxy-4-methoxybenzophenone, 2-hydroxy-4-methoxy-4'-methylbenzophenone, and 2,2'-dihydroxy-4-methoxybenzophenone;

esters of benzyl malonic acid, preferably 4-methoxybenzyl malonic acid di-2-ethylhexyl-ester;

triazine derivatives, such as e.g. 2,4,6-trianilino-(p-carbo-2'-ethyl-1'-hexyloxy)-1,3,5-triazine and octyl triazone or dioctyl butamidotriazone (Uvasorb® HEB);

propane-1,3-diones, such as e.g. 1-(4-tert-butylphenyl)-3-(4'methoxyphenyl)propane-1,3-dione;

ketotricyclo(5.2.1.0)decane derivatives.

Suitable water-soluble substances include:

2-phenylbenzimidazole-5-sulfonic acid and alkali, alkaline earth, ammonium, alkyl ammonium, alkanolammonium and glucammonium salts thereof;

1H-benzimidazole-4,6-disulfonic acid, 2,2'-(1,4-phenylene)bis, disodium salt (Neo Heliopan® AP)

sulfonic acid derivatives of benzophenones, preferably 2-hydroxy-4-methoxybenzo-phenone-5-sulfonic acid and salts thereof;

sulfonic acid derivatives of 3-benzylidene camphor, such as e.g. 4-(2-oxo-3-bornylidene methyl)benzenesulfonic acid and 2-methyl-5-(2-oxo-3-bornylidene)sulfonic acid and salts thereof.

In particular, suitable UVA filters include derivatives of benzoyl methane, such as e.g. 1-(4'-tert-butylphenyl)-3-(4'-methoxyphenyl)propane-1,3-dione, 4-tert-butyl-4'-methoxydibenzoyl methane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione and enamine compounds. The UVA and UVB filters can of course also be used in mixtures. Particularly favorable combinations are composed of the derivatives of benzoylmethane, e.g. 4-tert-butyl-4'-methoxydibenzoylmethane (Parsol® 1789) and 2-cyano-3,3-phenylcinnamic acid-2-ethyl-hexyl ester (octocrylene) in combination with esters of cinnamic acid, preferably 4-methoxycinnamic acid-2-ethylhexyl ester and/or 4-methoxycinnamic acid propyl ester and/or 4-methoxycinnamic acid isoamyl ester. Advantageously, these combinations are used together with water-soluble filters such as e.g. 2-phenylbenzimidazole-5-sulfonic acid and alkali, alkaline earth, ammonium, alkylammoium, alkanolammonium- and glucammonium salts thereof.

In addition to the above-mentioned soluble substances, insoluble light protection pigments, specifically finely-dispersed metal oxides or salts, are also suitable for this purpose. Examples of suitable metal oxides are in particular zinc oxide and titanium dioxide, as well as oxides of iron, zirconium, silicon, manganese, aluminum and cerium and mixtures thereof. Silicates (talc), barium sulfate or zinc stearate may be used as salts. The oxides and salts are used in the form of pigments for skin care and skin protection emulsions and decorative cosmetics. In this case, the particles should have an average diameter of less than 100 nm, preferably 5 to 50 nm and in particular 15 to 30 nm. They can have a spherical shape, but particles may also be used that have an ellipsoid shape or another form deviating from the spherical shape. The pigments can also be present in surface-treated, i.e. hydrophilized or hydrophobized form. Typical examples are coated titanium dioxides, such as e.g. titanium dioxide T 805 (Degussa) or Eusolex® T2000, Eusolex® T, Eusolex® T-ECO, Eusolex® T-Aqua, Eusolex® T-45D (all Merck), Uvinul $TiO_2$ (BASF). In this context, suitable hydrophobic coating agents are primarily silicones, specifically trialkoxyoctylsilanes or simethicones. In sun protection agents, so-called micro- or nanopigments are preferably used. Preferably, a micronized zinc oxide such as e.g. Z-COTE® or Z-COTE HP1® is used.

Humectants

Humectants serve to further optimize the sensory properties of the composition and to regulate moisture on the skin. At the same time, the low-temperature stability of the preparations according to the invention, in particular in the case of emulsions, is increased. The humectants are ordinarily comprised in an amount of 0.1 to 15 wt %, preferably 1 to 10 wt %, and in particular 5 to 10 wt %.

Humectants preferred according to the invention include amino acids, pyrrolidone carboxylic acid, lactic acid and salts thereof, lactitol, urea and urea derivatives, uric acid, glucosamine, creatinine, cleavage products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexane triol, polyethylene glycols such as PEG-4, PEG-6, PEG-7, PEG-8, PEG-9, PEG-10, PEG-12, PEG-14, PEG-16, PEG-18, PEG-20), sugar and sugar derivatives (including fructose, glucose, maltose, maltitol, mannitol, inositol, sorbitol, sorbitol silane diol, sucrose, trehalose, xylose, xylitol, glucuronic acid and salts thereof), ethoxylated sorbitol (Sorbeth-6, Sorbeth-20, Sorbeth-30, Sorbeth-40), honey and hardened honey, hardened starch hydrolysates and mixtures of hardened wheat protein and PEG-20-acetate copolymer. Preferred according to the invention as suitable humectants are glycerol, diglycerol, triglycerol and butylene glycol.

Biogenic Agents and Antioxidants

Biogenic agents are understood for example to refer to tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts such as e.g. prune extract, Bambara nut extract and vitamin complexes.

Antioxidants disrupt the photochemical reaction chain that is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides such as D,L carnosine, D carnosine, L carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cysteamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximine, homocysteine sulfoximine, buthionine sulfone, penta-, hexa-, heptathionine sulfoximine) in very low tolerable dosages (e.g. pmol to µmol/kg), further (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin-A-palmitate) and coniferyl benzoate from benzoic resin, rutinic acid and derivatives thereof, α-glycosylrutin, ferulic acid, furfurylidene glucitol, carnosine, butylhydroxytoluene, butylhydroxyanisole, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenium methionine), stilbenes and derivatives thereof (e.g. stilbene oxide, trans-stilbene oxide) and suitable derivatives according to the invention of the above-mentioned agents (salts, esters, ethers, sugars, nucleotides, nucleosides, peptides and lipids).

Deodorants and Antimicrobial Agents

Cosmetic deodorants (deodorizing agents) counteract body odors or mask or eliminate them. Body odors occur due to the effect of skin bacteria on apocrine perspiration, wherein unpleasant-smelling decomposition products are formed. Accordingly, deodorants comprise agents that function as antimicrobial agents, enzyme inhibitors, odor absorbers, and odor-asking agents.

Antimicrobial Agents.

As antimicrobial agents, all substances active against gram-positive bacteria are generally suitable, such as e.g. 4-hydroxybenzoic acid and salts and esters thereof, N-(4-chlorophenyl)-N'(3,4-dichlorophenyl)urea, 2,4,4'-trichloro-2'-hydroxy-di-phenylether (triclosan), 4-chloro-3,5-dimethylphenol, 2,2'-methylene-bis(6-bromo-4-chlorophenol), 3-methyl-4-(1-methylethyl)-phenol, 2-benzyl-4-chlorophenol, 3-(4-chlorophenoxy)-1,2-propanediol, 3-iodo-2-propinylbutylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DMC), salicylic acid-N-alkylamides such as e.g. salicylic acid-n-octylamide or salicylic acid-n-decylamide.

Enzyme Inhibitors.

Examples of suitable enzyme inhibitors are esterase inhibitors. These are preferably trialkyl citrates such as trimethyl citrate, tripropyl citrate, triisopropyl citrate, tributyl citrate and in particular triethyl citrate (Hydagen® CAT). These substances inhibit enzyme activity and thus reduce the formation of odors. Further substances suitable as esterase inhibitors are sterol sulfates or phosphates, such as e.g. lanosterol, cholesterol, campesterol, stigmasterol and sitosterol sulfates or phosphates, dicarboxylic acids and esters thereof, such as e.g. glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof such as e.g. citric acid, malic acid, tartaric acid or tartaric acid diethyl ester, and zinc glycinate.

Odor Absorbers.

Suitable as odor absorbers are substances that are capable of absorbing odor-causing compounds and largely retaining them. They reduce the partial pressure of the individual components and thus reduce their rate of diffusion. It is important in this case that perfumes must remain unaffected. Odor absorbers have no effect against bacteria. They comprise for example as the main component a complex zinc salt of ricinoleic acid or special, largely odor-neutral fragrances that are known to the person having ordinary skill in the art as "fixators," such as e.g. extracts of labdanum or styrax or certain abietic acid derivatives. Fragrances or perfume oils that, in addition to their function as odor-masking agents, provide deodorants with their respective scents act as odor-masking agents. Examples of perfume oils that can be mentioned are mixtures of natural and synthetic fragrances. Natural fragrances are extracts of flowers, stems and leaves, fruits, fruit peels, roots, woods, hers and grasses, needles and branches, and resins and balsams. Also suitable are animal raw materials such as e.g. civet and castoreum. Typical synthetic fragrance compounds are products of the ester, ether, aldehyde, ketone, alcohol and hydrocarbon types. Fragrance compounds of the ester type are e.g. benzyl acetate, p-tert-butylcyclohexyl acetate, linalyl acetate, phenethyl acetate, linalyl benzoate, benzyl formiate, allylcyclohexyl propionate, styrallyl propionate and benzyl salicylate. Examples of ethers include benzyl ethyl ether, and examples of aldehydes include linear alkanals with 8 to 18 carbon atoms, citral, citronellal, citronellyl oxyacetaldehyde, cyclamen aldehyde, hydroxycitronellal, lilial and bourgeonal, examples of ketones include the ionones and methyl cedryl ketone, alcohols include anethol, citronellol, eugenol, isoeugenol, geraniol, linalool, phenethyl alcohol and terpineol, and hydrocarbons include mainly the terpenes and balsams. Preferred, however, are mixtures of various fragrances that together produce a pleasant scent. Essential oils of low volatility, which are usually used as flavoring components, are also suitable as perfume oils, e.g. sage oil, chamomile oil, clove oil, Melissa oil, mint oil, cinnamon leaf oil, linden flower oil, juniper berry oil, vetiver oil, olibanum oil, galbanum oil, labdanum oil and lavandin oil. Preferred are bergamot oil, dihydromyrcenol, lilial, lyral, citronellol, phenethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-Damascone, geranium oil bourbon, cyclohexyl salicylate, Vertofix Coeur, iso-E-super, Fixolide NP, evernyl, iraldein gamma, phenylacetic acid, geranyl acetate, benzyl acetate, rose oxide, Romilat, Irotyl and Floramat are used alone or in mixtures.

Antiperspirants.

Antiperspirants (antiperspirant agents) reduce the formation of perspiration by affecting the activity of the eccrine sweat glands, thus counteracting underarm wetness and body odor. Aqueous or anhydrous formulations of antiperspirants typically comprise the following ingredients:

astringent agents,
oil components,
nonionic emulsifiers,
coemulsifiers,
bodying agents,
excipients such as e.g. thickeners or complexing agents and/or
non-aqueous solvents such as e.g. ethanol, propylene glycol and/or glycerol.

Suitable as astringent antiperspirant agents are primarily salts of aluminum, zirconium or zinc. Examples of such suitable antihydrotically active agents are e.g. aluminum chloride, aluminum chlorohydrate, aluminum dichlorohydrate, aluminum sesquichlorohydrate and complex compounds thereof, e.g. with propylene glycol-1,2-aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids such as glycine. In addition, antiperspirants may comprise common oil-soluble and water-soluble excipients in small amounts. Such oil-soluble excipients can for example include:

anti-inflammatory, skin-protective, or fragrant essential oils,
synthetic skin-protective agents and/or
oil-soluble perfume oils.

Common water-soluble additives are e.g. preservatives, water-soluble fragrances, pH-adjusting agents, e.g. buffer mixtures, water-soluble thickeners, e.g. water-soluble natural or synthetic polymers such as e.g. xanthan gum, hydroxyethylcellulose, polyvinylpyrrolidone or high molecular weight polyethylene oxides.

Film-Forming Agents

Common film-forming agents are for example chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acids or salts thereof and similar compounds.

Anti-Dandruff Agents

Suitable anti-dandruff agents are piroctone olamine (1-hydroxy-4-methyl-6-(2,4,4-trimythylpentyl)-2-(1H)-pyridinone monoethanolamine salt), Baypival® (climbazole), Ketoconazol®, (4-acetyl-1-{-4-[2-(2,4-dichlorphenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur-tar distillates, salicylic acid (or in combination with hexachlorophene), undecylenic acid monoethanolamide sulfosuccinate Na-salt, Lamepon® UD (protein-undecylenic acid condensate), zinc pyrithione, aluminum pyrithione and magnesium pyrithione/dipyrithione-magnesium sulfate.

Swelling Agents

Montmorillonite, clay mineral substances, Pemulen and alkyl-modified Carbopol grades (Goodrich) can serve as swelling agents for aqueous phases. Further suitable polymers or swelling agents can be found in the overview by R. Lochhead in Cosm. Toil. 108, 95 (1993).

Insect Repellents

Suitable insect repellents are N,N-diethyl-m-toluamide, 1,2-pentanediol or ethyl butyl acetyl aminopropionate.

Self-Tanning Agents

Dihydroxyacetone is suitable as a self-tanning agent. Examples of suitable tyrosine inhibitors, which prevent the formation of melanin and are used in depigmenting agents, include arbutin, ferulic acid, kojic acid, coumaric acid and ascorbic acid (vitamin C).

Hydrotropes

In order to improve flow behavior, one can further add hydrotropes, such as e.g. ethanol, isopropyl alcohol, or polyols; these substances are largely equivalent to the above-mentioned carriers. Suitable polyols in this context preferably have 2 to 15 carbon atoms and at least two hydroxyl groups. The polyols can also comprise further functional groups, in particular amino groups, or be modified with nitrogen. Typical examples are glycerol;
alkylene glycols, such as e.g. ethylene glycol, diethylene glycol, propylene glycol, butylene glycol, hexylene glycol and polyethylene glycols with an average molecular weight of 100 to 1,000 g/mol;
technical oligoglycerol mixtures with a degree of autocondensation of 1.5 to 10 such as e.g. technical diglycerol mixtures with a diglycerol content of 40 to 50 wt %;
methyol compounds, such as in particular trimethylol ethane, trimethylol propane, trimethylol butane, pentaerythritol and dipentaerythritol;
lower alkyl glucoses, in particular those with 1 to 8 carbons in the alkyl radical, such as e.g. methyl and butyl glycoside;
sugar alcohols with 5 to 12 carbon atoms, such as e.g. sorbitol or mannitol,
sugars with 5 to 12 carbon atoms, such as e.g. glucose or saccharose;
amino sugars, such as e.g. glucamine;
dialcohol amines, such as diethanolamine or 2-amino-1, 3-propanediol.

Preservatives

Examples of suitable preservatives include phenoxyethanol, formaldehyde solution, parabens, pentanediol or sorbic acid, the silver complexes known under the name Surfacine®, and the further substance classes listed in Appendix 6, Parts A and B of the Cosmetics Ordinance.

Dyes

Substances suitable and approved for cosmetic purposes, such as those listed for example in the publication "Kosmeticsche Färbemittel [Cosmetic Dyes]" of the Farbstoffkommission der Deutschen Forschungsgemeinschaft [Dye Commission of the German Research Foundation], Verlag Chemie, Weinheim, 1984, pp. 81-106, may be used as dyes. Examples are cochineal red A (CI 16255), patent blue V (CI 42051), indigotin (CI 73015), chlorophyllin (CI 75810), choline yellow (CI 47005), titanium dioxide (CI 77891), indanthrene blue RS (CI 69800) and alizarin red (CI 58000). Luminol can also be included as a luminescent dye. These dyes are ordinarily used in concentrations of 0.001 to 0.1 wt %, based on the amount of the entire mixture.

The total content of the excipients and additives can be 1 to 50, preferably 5 to 40 wt %, based on the agents. The agents can be produced by means of common cold or hot processes; the phase inversion temperature method is preferably used.

Detergents, Rinsing Agents, and Cleaning Agents

Detergents, rinsing agents, and cleaning agents in the context of the present invention are preferably in the form of liquids, solids, gels, pastes, or powders. These are preferably detergents that are suitable for both manual and machine washing, in particular of textiles. They can also be detergents or cleaning agents for industrial or household use. For example, cleaning agents can also be used for cleaning hard surfaces. They can be dishwashing agents used for manual or machine washing of dishes. They can also be the usual industrial or household cleaners used to clean hard surfaces such as furniture surfaces, slabs and tiles, and wall and floor coverings. In addition to dishes, all other hard surfaces in household or industrial applications, made in particular of glass, ceramics, plastic, or metal, are suitable.

The detergents, rinsing agents, and cleaning agents can further comprise commercially available components, such as e.g. surfactants, builders, bleaching agents, bleaching agent activators, thickeners, enzymes, electrolytes, pH-adjusting agents, dyes and fragrances, foam inhibitors, anti-redeposition agents, optical brighteners, greying inhibitors, anti-creasing agents, antimicrobial agents, preservatives, antioxidants, antistatics, UV adsorbers, heavy metal complexing agents and the like. These excipients are described in further detail below:

Surfactants

As surfactants for the production of the detergents or cleaning agents, in addition to the nonionic surfactants, anionic, cationic, amphoteric and/or nonionic surfactants and branched alkyl sulfates can also be used.

As nonionic surfactants, alkoxylated, preferably ethoxylated, in particular primary alcohols, preferably with 8 to 18 C atoms and an average of 1 to 12 mol of ethylene oxide (EO) per mol of alcohol, are used, in which the alcohol radical can be linear or preferably methyl-branched at the 2 position or can comprise linear and methyl-branched radicals in the mixture, such as those ordinarily present in oxo alcohol radicals. However, alcohol ethoxylates with linear radicals of alcohols of native origin with 12 to 18 C atoms, for example of coconut, palm, tallow fatty or oleyl alcohol and an average of 2 to 8 mol of EO per mol of alcohol are particularly preferred. Examples of preferred ethoxylated alcohols include $C_{12-14}$ alcohols with 3, 4, or 7 mol of EO, $C_{9-11}$ alcohol with 7 mol of EO, $C_{13-5}$ alcohols with 3, 5, 7, or 8 mol of EO, $C_{12-18}$ alcohols with 3, 5, or 7 mol of EO and mixtures thereof, such as mixtures of $C_{12-4}$ alcohol with 3 mol of EO and $C_{12-8}$ alcohol with 7 mol of EO. The indicated degrees of ethoxylation constitute statistical mean values that can be a whole number or a fraction for a particular product. Preferred alcohol ethoxylates show a narrow homolog distribution (narrow-range ethoxylates, NRE). In addition to these nonionic surfactants, fatty alcohols with more than 12 mol of EO can also be used. Examples are tallow fatty alcohols with 14, 25, 30, or 40 mol of EO. Nonionic surfactants comprising EO and PO groups together in the molecule can also be used according to the invention. In this case, block copolymers with EO-PO block units or PO-EO block units may be used, but also EO-PO-EO copolymers or PO-EO-PO copolymers. Of course, mixed alkoxylated nonionic surfactants in which the EO and PO units are distributed not blockwise, but statistically, can also be used. Such products can be obtained by means of the simultaneous action of ethylene and propylene oxide on fatty alcohols.

A further class of nonionic surfactants that can be advantageously used for producing detergents or cleaning agents are the alkyl polyglycosides (APG). Usable alky polyglycosides meet the general formula RO(G)Z, in which R denotes a saturated or unsaturated aliphatic radical with 8 to 22, and preferably 12 to 18 C atoms that is linear or branched, in particular methyl-branched at the 2 position, and G is the symbol for a glycolysis unit with 5 or 6 C atoms, preferably glucose. Here, the degree of glycosidation is between 1.0 and 4.0, preferably between 1.0 and 2.0, and in particular between 1.1 and 1.4.

Nonionic surfactants of the amine oxide type, for example N-coconut alkyl-N,N-dimethylamine oxide and N-tallow alkyl-N,N-dihydroxyethyl amine oxide, and the fatty acid alkanolamides, can also be suitable for producing the detergents or cleaning agents. The amount of these nonionic surfactants is preferably not more than that of the ethoxylated fatty alcohols, in particular not more than half thereof.

Further suitable surfactants are polyhydroxy fatty acid amides of the formula

R—CO—N(R1)-[Z], in which RCO denotes an aliphatic acyl radical with 6 to 22 carbon atoms, R1 hydrogen, an alkyl or hydroxyalkyl radical with 1 to 4 carbon atoms and [Z] a linear or branched polyhydroxyalkyl radical with 3 to 10 carbon atoms and 3 to 10 hydroxyl groups. The polyhydroxy fatty acid amides are known substances that can ordinarily be obtained by reductive amination of a reducing sugar with ammonia, an alkylamine, or an alkanolamine and subsequent acylation with a fatty acid, a fatty acid alkyl ester or a fatty acid chloride. The group of the polyhydroxy fatty acid amides also includes compounds of the formula R—CO—N(R1-O—R2)-[Z], in which R denotes a linear or branched alkyl or alkenyl radical with 7 to 12 carbon atoms, R1 a linear, branched or cyclic alkyl radical or an aryl radical with 2 to 8 carbon atoms and R2 a linear, branched or cyclic alkyl radical or an aryl radical or an oxoalkyl radical with 1 to 8 carbon atoms, wherein $C_{1-4}$ alkyl or phenyl radicals are preferred, and [Z] denotes a linear polyhydroxyalkyl radical whose alkyl chain is substituted with at least two hydroxyl groups or alkoxylated, preferably ethoxylated or propoxylated derivatives of this radical. [Z] is preferably obtained by reductive amination of a sugar, for example glucose, fructose, maltose, lactose, galactose, mannose or xylose. The N-alkoxy or N-aryloxy-substituted compounds can then be converted to the desired polyhydroxy fatty acid amide by means of a reaction with fatty acid methyl esters in the presence of an alkoxide as a catalyst.

The content of nonionic surfactants in the liquid detergents and cleaning agents is preferably 5 to 30 wt %, more preferably 7 to 20 wt % and in particular 9 to 15 wt %, based in each case on the agent as a whole.

Examples of anionic surfactants include those of the sulfonate and sulfate type. Here, preferred surfactants of the sulfonate type are $C_{9-3}$ alkylbenzene sulfonates, olefin sulfonates, i.e. mixtures of alkene and hydroxyalkane sulfonates and disulfonates, such as can be obtained from $C_{12-8}$ monoolefins with a terminal or internal double bond by sulfonation with gaseous sulfur trioxide and subsequent alkaline or acidic hydrolysis of the sulfonation products. Also suitable are alkane sulfonates, which are obtained from $C_{12-8}$ alkanes, for example by sulfochlorination or sulfoxidation with subsequent hydrolysis or neutralization. Also suitable are the esters of α-sulfo fatty acids (ester sulfonates), for example the α-sulfonated methyl esters of hydrogenated coconut, palm kernel or tallow fatty acids.

Also suitable are sulfonation products of unsaturated fatty acids, for example oleic acid, in small amounts, preferably in amounts of not more than approximately 2 to 3 wt %. Particularly preferred are α-sulfo fatty acid alkyl esters having an alkyl chain with not more than 4 C atoms in the ester group, for example methyl esters, ethyl esters, propyl esters and butyl esters. The methyl esters of α-sulfo fatty acids (MES), but also saponified disalts thereof, are used particularly advantageously.

As further anionic surfactants, fatty acid derivatives of amino acids, for example of N-methyl taurine (taurides) and/or N-methyl glycine (sarcosides) are suitable. Particularly preferred in this case are the sarcosides or the sarcosinates, above all sarcosinates of higher and optionally mono- or polyunsaturated fatty acids such as oleyl sarcosinates.

Further suitable anionic surfactants are sulfonated fatty acid glycerol esters. The term fatty acid glycerol esters is understood to refer to mono, di- and triesters and mixtures thereof, such as those obtained in production by esterification of a monoglycerol with 1 to 3 mol of fatty acid or esterification of triglycerides with 0.3 to 2 mol of glycerol. Preferred sulfonated fatty acid glycerol esters are the sulfonation products of saturated fatty acids with 6 to 22 carbon atoms, for example caproic acid, caprylic acid, capric acid, myristic acid, lauric acid, palmitic acid, stearic acid or behenic acid.

Preferred as alk(en)yl sulfates are the alkali and in particular sodium salts of sulfuric acid semi-esters of the $C_{12}$-$C_{18}$ fatty alcohols, for example coconut fatty alcohol, tallow fatty alcohol, lauryl, myristyl, cetyl or stearyl alcohol or the $C_{10}$-$C_{20}$ oxo alcohols and semi-esters of secondary alcohols of these chain lengths. Also preferred are alk(en)yl sulfates of the above-mentioned chain length comprising a synthetic linear alkyl radical produced on a petrochemical basis that shows degradation behavior analogous to the suitable compounds based on fatty chemical raw materials. Of interest from the standpoint of washing technology, the $C_{12}$-$C_{16}$ alkyl sulfates, $C_{12}$-$C_{15}$ alkyl sulfates, and $C_{14}$-$C_{15}$-alkyl sulfates are preferred. 2,3-alkyl sulfates, which can be obtained as commercial products of Shell Oil Company under the name DAN®, are also suitable anionic surfactants.

Also suitable are sulfuric acid monoesters of linear or branched $C_{7-21}$ alcohols ethoxylated with 1 to 6 mol of ethylene oxide, such as 2-methyl-branched $C_{9-11}$ alcohols having an average of 3.5 mol of ethylene oxide (EO) or $C_{12-18}$ fatty alcohols with 1 to 4 mol of EO. Because of their strong foaming capacity, they are used in cleaning agents only in relatively small amounts, for example in amounts of 1 to 5 wt %.

Further suitable anionic surfactants are also the salts of alkyl sulfosuccinic acid, which are also referred to as sulfosuccinates or sulfosuccinic acid esters, and constitute monoesters and/or diesters of sulfosuccinic acid with alcohols, preferably fatty alcohols and in particular ethoxylated fatty alcohols. Preferred sulfosuccinates comprise $C_{8-18}$ fatty alcohol radicals or mixtures thereof. Particularly preferred sulfosuccinates comprise a fatty alcohol radical derived from ethoxylated fatty alcohols, which considered in isolation constitute nonionic surfactants (see description below). In this context, sulfosuccinates whose fatty alcohol radicals are derived from ethoxylated fatty alcohols with a narrow homolog distribution are again particularly preferred. It is also possible to use alk(en)yl succinic acid, preferably with 8 to 18 carbon atoms in the alk(en)yl chain, or salts thereof.

Particularly preferred anionic surfactants are soaps. Suitable are saturated and unsaturated fatty acid soaps such as the salts of lauric acid, myristic acid, palmitic acid, stearic acid, (hydrogenated) erucic acid and behenic acid and in particular soap mixtures derived from natural fatty acids, for example coconut, palm kernel oil, olive oil, or tallow fatty acids.

The anionic surfactants including the soaps can be present in the form of sodium, potassium or ammonium salts thereof and as soluble salts or organic bases such as mono-, di- or triethanolamine. Preferably, the anionic surfactants are in the form of sodium or potassium salts, in particular sodium salts, thereof.

The content in preferred liquid detergents and cleaning agents of anionic surfactants is 1 to 30 wt %, preferably 4 to 25 wt % and in particular 5 to 22 wt %, based in each case on the agent as a whole. Particularly preferably, the amount of fatty acid soaps is at least 2 wt %, more preferably at least 3 wt %, and most preferably at least 4 wt %.

As further surfactants, so-called gemini surfactants are suitable for the production of the detergents or cleaning agents according to the invention. These are generally understood to include compounds that have two hydrophilic groups and two hydrophobic groups per molecule. These groups are ordinarily separated from one another by a so-called "spacer." As a rule, this spacer is a carbon chain that should be long enough to allow the hydrophilic groups to be at a sufficient distance from one another so that they can act in a mutually independent manner. Such surfactants are generally characterized by an unusually low critical micelle concentration and the capacity to sharply reduce the surface tension of water. In exceptional cases, however, the term gemini surfactants is understood to refer not only to dimeric, but also to trimeric surfactants.

Gemini surfactants for producing detergents or cleaning agents are for example sulfated hydroxy mixed ethers according to the German Patent Application DE-A 4321022 or dimer alcohol bis- and trimer alcohol-tris sulfates and -ether sulfates according to the German Patent Application DE-A 19503061. End-capped dimer and trimer mixed eithers according to the German Patent Application DE-A 19513391 are characterized in particular by their bi- and multifunctionality. The above-mentioned end-capped surfactants thus have good network properties and also generate little foam, so that they are particularly suitable for use in machine detergent or cleaning methods.

Preferred from an application technology standpoint are mixtures of anionic and nonionic surfactants. The total surfactant content of the liquid detergents and cleaning agents is preferably less than 40 wt %, and particularly preferably less than 35 wt %, based on the total amount of liquid detergents and cleaning agents.

Builders

Particular examples to be mentioned of builders or builder substances that can be contained in the liquid detergents and cleaning agents are silicates, aluminum silicates (in particular zeolites), carbonates, organic cobuilders, phosphates, salts of organic di- and polycarboxylic acids and mixtures of these substances.

Suitable crystalline layered sodium silicates have the general formula NaMSi$_x$O$_{2x+1}$*H$_2$O, where M denotes sodium or hydrogen, x is a number from 1.9 to 4 and y is a number from 0 to 20, with preferred values for x being 2, 3 or 4. Preferred crystalline layer silicates of the indicated formula are those in which M denotes sodium and x takes the values 2 or 3. In particular, both β- and δ-sodium disilicates Na$_2$Si$_2$O$_5$*yH$_2$O are preferred.

Also suitable for use are amorphous sodium silicates with an Na$_2$O:SiO$_2$ modulus of 1:2 to 1:3.3, preferably 1:2 to 1:2.8, and in particular 1:2 to 1:2.6 that are slow-dissolving and show secondary washing properties. In this case, dissolution can be delayed compared to conventional amorphous sodium silicates in various ways, for example by surface treatment, compounding, compacting/compression or overdrying. In the context of this invention, the term "amorphous" is also understood to mean "x-ray amorphous." This means that in x-ray diffraction experiments, the silicates do not yield the sharp x-ray reflexes typical of crystalline substances, but at most one or more maxima of the scattered x-ray radiation that show a width of several degree units of the diffraction angle. However, even highly favorable builder properties can very well be obtained if the silicate particles yield washed-out or even sharp diffraction maxima in electron diffraction experiments. This is to be interpreted as indicating that the products show microcrystalline areas on the order of 10 to several hundred nm, wherein values of up to at most 50 nm and in particular up to at most 20 nm are preferred. Such so-called x-ray amorphous silicates also show delayed dissolution compared to conventional water glasses. Particularly preferred are compressed/compacted amorphous silicates, compounded amorphous silicates and overdried x-ray amorphous silicates.

A fine crystalline and synthetic zeolite comprising bound water that is suitable for use is preferably zeolite A and/or P. Zeolite MAP™ (commercial product from Crosfield) is particularly preferred as zeolite P. However, zeolite X and mixtures of zeolite A, X and/or P are also suitable. An example of a commercially available substance that can preferably be used in the context of the present invention is a cocrystallate of zeolite X and zeolite A (approx. 80 wt % zeolite X), which is sold by SASOL under the brand name VEGOBOND AX® and can be described by the formula

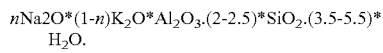
$n$Na2O*(1-$n$)K$_2$O*Al$_2$O$_3$.(2-2.5)*SiO$_2$.(3.5-5.5)*H$_2$O.

The zeolite may be used as a spray-dried powder or as an undried stabilized suspension that is still wet before being produced. In cases where the zeolite is used as a suspension, it can comprise small amounts of additives to nonionic surfactants as stabilizers, for example 1 to 3 wt % based on zeolite of ethoxylated C$_{12}$-C$_{18}$ fatty alcohols with 2 to 5 ethylene oxide groups, C$_{12}$-C$_{14}$ fatty alcohols with 4 to 5 ethylene oxide groups, or ethoxylated isotridecanols. Suitable zeolites show an average particle size of less than 10 µm (volume distribution; measurement method: Coulter counter) and preferably comprise 18 to 22 wt %, in particular 20 to 22 wt % of bound water.

Of course, it is also possible to use the generally-known phosphates as builders, provided such use is not to be avoided for ecological reasons. In particular, sodium salts of the orthophosphates, pyrophosphates, and in particular tripolyphosphates are suitable.

Suitable as builders are organic cobuilders, in particular polycarboxylate/polycarboxylic acids, polymeric polycarboxylates, aspartic acid, polyacetals, dextrins, and phosphonates.

Examples of polymeric polycarboxylates include the alkali metal salts of polyacrylic acid or polymethacrylic acid, for example those with a relative molecular weight of 500 to 70,000 g/mol. Within the meaning of this document, the molecular weights given for polymeric polycarboxylates are weight-average molecular weights Mw of the respective acid form, which were generally determined by gel permeation chromatography (GPC), wherein a UV detector was used. In this case, measurement was carried out against an external polyacrylic acid standard, which yields realistic molecular weight values because it is structurally related to the polymers studied. These indications deviate significantly from the molecular weights given when polystyrene sulfonic acids are used as a standard. As a rule, the molecular weights measured against polystyrene sulfonic acids are significantly higher than those given in this document.

Suitable polymers are in particular polyacrylates, which preferably have a molecular weight of 2,000 to 20,000 g/mol. Among this group, because of their superior solubility, the short-chain polyacrylates, which show molecular weights of 2,000 to 10,000 g/mol, and particularly preferably 3,000 to 5,000 g/mol, can again be preferable.

Also suitable are copolymeric polycarboxylates, in particular of acrylic acid with methacrylic acid and acrylic acid or methacrylic acid with maleic acid. Copolymers of acrylic acid with maleic acid comprising 50 to 90 wt % acrylic acid and 50 to 10 wt % maleic acid have been found to be particularly suitable. Their relative molecular weight based on free acids is generally 2,000 to 70,000 g/mol, preferably 20,000 to 50,000 g/mol and in particular 30,000 to 40,000 g/mol.

Particularly preferred are also biodegradable polymers of more than two different monomer units, for example those comprising salts of acrylic acid and of maleic acid and vinyl alcohol or vinyl alcohol derivatives as monomers or those comprising salts of acrylic acid and 2-alkylallylsulfonic acid and sugar derivatives as monomers.

Further preferred copolymers are those preferably comprising acrolein and acrylic acid/acrylic acid salts or acrolein and vinyl acetate as monomers.

Polymeric aminodicarboxylic acids, salts thereof or their precursors can also be mentioned as further preferred builders. Particularly preferred are polyaspartic acids or salts thereof and derivatives that also have a bleach-stabilizing action in addition to their properties as cobuilders.

Further suitable builders are polyacetals, which can be obtained by reacting dialdehydes with polyol carboxylic acids that have 5 to 7 C atoms and at least 3 hydroxyl groups. Preferred polyacetals are obtained from dialdehydes such as glyoxal, glutaraldehyde, terephthalaldehyde and mixtures thereof and from polyol carboxylic acids such as gluconic acid and/or glucoheptonic acid.

Further suitable organic builders are dextrins, for example oligomers or polymers of carbohydrates, which can be obtained by partial hydrolysis of starches. Hydrolysis can be carried out by common methods, for example acid or enzyme-catalyzed methods. The hydrolysis products preferably have average molecular weights in the range of 400 to 500,000 g/mol. In this context, a polysaccharide with a dextrose equivalent (DE) in the range of 0.5 to 40, in particular 2 to 30, is preferred, wherein DE is a common measure of the reducing action of a polysaccharide compared to dextrose, which has a DE of 100. Both maltodextrins with a DE of between 3 and 20 and dry glucose syrups with a DE of between 20 and 37 and so-called yellow dextrins and white dextrins with higher molecular weights in the range of 2,000 to 30,000 g/mol may be used.

The oxidized derivatives of such dextrins are their reaction products with oxidizing agents that are capable of oxidizing at least one alcohol functional group of the saccharide ring to the carboxylic acid functional group. A product oxidized on C6 of the saccharide ring can be particularly advantageous.

A preferred dextrin is described in the British Patent Application GB 9,419,091 B1. The oxidized derivatives of such dextrins are their reaction products with oxidizing agents that are capable of oxidizing at least one alcohol functional group of the saccharide ring to the carboxylic acid functional group. Such oxidized dextrins and methods for their production are known for example from the European Patent Applications EP 032202 A, EP 0427349 A, EP 0472042 A and EP 0542496 A and the International Patent Applications WO 1992/018542 A, WO 1993/008251 A, WO 1994/028030 A, WO 1995/007303 A, WO 1995/012619 A and WO 1995/020608 A. A product oxidized on $C_6$ of the saccharide ring can be particularly advantageous.

Oxydisuccinates and other derivatives of disuccinates, preferably ethylene diamine disuccinate, are also suitable cobuilders. In this context, ethylene diamine-N,N'-disuccinate (EDDS), preferably in the form of its sodium or magnesium salts, is used. Also preferred in this context are glycerol disuccinates and glycerol trisuccinates, as described for example in the U.S. Pat. No. 4,524,009, 4,639,325, the European Patent Application EP 0150930 A and the Japanese Patent Application JP 1993/339896 A.

Further suitable organic cobuilders are for example acetylated hydroxycarboxylic acids or salts thereof, which can also optionally be present in lactone form and which comprise at least 4 carbon atoms, at least one hydroxy group, and at most two acid groups. Such cobuilders are described for example in the International Patent Application WO 1995/020029 A.

A further substance class with cobuilder properties is represented by the phosphonates. In particular, these are hydroxyalkane or aminoalkane phosphonates. Among the hydroxyalkane phosphonates, 1-hydroxyethane-1,1-diphosphonate (HEDP) is of particular importance as a cobuilder. It is preferably used as sodium salt, wherein the disodium salt reacts neutrally and the tetrasodium salt in an alkaline manner (pH 9). As aminoalkane phosphonates, ethylene diamine tetramethylene phosphonate (EDTMP), diethylene triamine pentamethylene phosphonate (DTPMP) and their higher homologs are preferably used. They are preferably used in the form of the neutrally reacting sodium salts, e.g. as hexasodium salt of EDTMP or as hepta- and octasodium salt of DTPMP. In this context, among the class of phosphonates, HEDP is preferably used as a builder. In addition, the aminoalkane phosphonates have a pronounced capacity to bind heavy metals. Accordingly, it may be preferred, in particular if the detergents and cleaning agents also comprise bleaches, to use aminoalkane phosphonates, in particular DTPMP, or mixtures of the above-mentioned phosphonates to produce the agents.

Moreover, all compounds capable of forming complexes with alkaline earth ions may be used as cobuilders.

Further usable organic builders are polycarboxylic acids that can also be used in the form of their sodium salts, wherein polycarboxylic acids are understood to refer to carboxylic acids bearing more than one acid functional group. For example, these include citric acid, adipic acid, succinic acid, glutaric acid, malic acid, tartaric acid, maleic acid, fumaric acid, saccharic acids, aminocarboxylic acids, nitrilotriacetic acid (NTA), provided such use is not objectionable for ecological reasons, and mixtures thereof. Preferred salts are salts of polycarboxylic acids such as citric acid, adipic acid, succinic acid, glutaric acid, tartaric acid, saccharic acids and mixtures thereof.

The acids per se can also be used. In addition to their builder action, acids typically also posses the property of an acidifying component and are thus also used for setting a lower and milder pH of detergents and/or cleaning agents. Particular examples that can be mentioned in this context are citric acid, succinic acid, glutaric acid, adipic acid, gluconic acid, and any desired mixtures thereof.

Bleaching Agents and Bleach Catalysts

Among the compounds serving as bleaching agents that yield $H_2O_2$ in water, sodium perborate tetrahydrate and sodium perborate monohydrate are of particular importance. Further useful bleaching agents are for example sodium percarbonate, peroxypyrophosphates, citrate perhydrates and $H_2O_2$-yielding peracidic salts or peracids such as perbenzoates, peroxophthalates, diperazelaic acid, phthaloiminoperacid or diperdodecanedioc acid. In order to achieve a better bleaching action in washing at temperatures of 60° C. and below, bleach activators can be incorporated into the detergents and cleaning agents. Compounds that yield aliphatic peroxocarboxylic acids, preferably with 1 to 10 C atoms, in particular 2 to 4 C atoms, and/or optionally substituted perbenzoic acid under perhydrolysis conditions can be used as bleach activators. Suitable are substances bearing O- and/or N-acyl groups with the above-mentioned number of C atoms and/or optionally substituted benzoyl groups. Preferred are polyacylated alkylene diamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoyl succinimide (NOSI), acylated phenol sulfonates, in particular N-nonanoyl or isononanoyl oxybenzene sulfonate (n- or iso-NOBS), carboxylic anhydrides, in particular phthalic acid anhydride, and acylated polyhydric alcohols, in particular triacetin, ethylene glycol diacetate and 2,5-diacetoxy-2,5-dihydrofuran. In addition to or instead of the conventional bleach activators, so-called bleach catalysts can also be incorporated into the textile treatment agents. These substances are bleach-enhancing transition metal salts or transition metal complexes such as e.g. Mn-, Fe-, Co-, R- or Mo-salen complexes or -carbonyl complexes. Mn-, Fe-, Co-, Ru-, Mo-, Ti-, V- and Cu-complexes with nitrogen-containing tripod ligands and Co-, Fe-, Cu- and Ru-ammine complexes can also be used as bleach catalysts.

Thickeners

A liquid detergent and cleaning agent may comprise a thickener. The thickener may for example be a polyacrylate thickener, xanthan gum, gellan gum, guar kernel flour, alginate, carrageenan, carboxymethylcellulose, bentonite, welan gum, locust bean flour, agar-agar, tragacanth, gum arabic, pectins, polyoses, starch, dextrins, gelatins and casein. However, modified natural substances such as modified starches and celluloses—here one can mention for example carboxymethylcellulose and other cellulose ethers, hydroxyethyl- and -propyl cellulose and locust bean gum ethers—can also be used as thickeners.

Examples of polyacrylic and polymethacrylic thickeners include the high molecular weight homopolymers of acrylic acid crosslinked with a polyalkenyl polyether, in particular an allyl ether of saccharose, pentaerythritol or propylene (INCI name according to the "International Dictionary of Cosmetic Ingredients" of "The Cosmetic, Toiletry and Fragrance Association (CTFA)": Carbomer), which are also referred to as carboxyvinyl polymers. Such polyacrylic acids include the products available from 3V Sigma under the name Polygel®, e.g. Polygel DA, and from B. F. Goodrich under the name Carbopol®, e.g. Carbopol 940 (molecular weight approx. 4,000,000 g/mol), Carbopol 941 (molecular weight approx. 1,250,000) or Carbopol 934 (molecular weight approx. 3,000,000 g/mol). Also included herein are the following acrylic acid copolymers: (i) copolymers of two or more monomers from the group of acrylic acid, methacrylic acid and their simple esters, preferably formed with $C_{1-4}$ alkanols (INCI: Acrylates Copolymer), including for example the copolymers of methacrylic acid, butyl acrylate and methyl methacrylate (CAS name according to Chemical Abstracts Service: 25035-69-2) or of butyl acrylate and methyl methacrylate (CAS 25852-37-3) and which for example are available from Rohm and Haas under the brand names Aculyn® and Acusol® and from Degussa (Goldschmidt) under the name Tego® Polymer, e.g. the anionic non-associative polymers Aculyn 22, Aculyn 28, Aculyn 33 (crosslinked), Acusol 810, Acusol 820, Acusol 823 and Acusol 830 (CAS 25852-37-3); (ii) crosslinked high molecular weight acrylic acid copolymers, including for example the copolymers, crosslinked with an allyl ether of saccharose or pentaerythritol, of $C_{10-30}$ alkyl acrylates with one or more monomers from the group of acrylic acid, methacrylic acid and their simple esters, preferably formed with $C_{1-4}$ alkanols (INCI: Acrylates/$C_{10-30}$ Alkyl Acrylate Crosspolymer), which are obtainable for example from B. F. Goodrich under the name Carbopol®, e.g. the hydrophobized Carbopol ETD 2623, Carbopol 1382 (INCI: Acrylates/$C_{10-30}$ Alkyl Acrylate Crosspolymer) and Carbopol Aqua 30 (formerly Carbopol EX 473).

A further polymeric thicker that is preferably to be used is xanthan gum, a microbial anionic heteropolysaccharide that is produced by *Xanthomonas campestris* and several other species under aerobic conditions and has a molecular weight of 2 to 15 million g/mol. Xanthan is composed of a chain of β-1,4-bound glucose (cellulose) with side chains. The structure of the subgroups is composed of glucose, mannose, glucuronic acid, acetate and pyruvate, wherein the number of pyruvate groups determines the viscosity of the xanthan gum. In particular, a fatty alcohol is also suitable as a thickener. Fatty alcohols can be branched or unbranched and can be of native or petrochemical origin. Preferred fatty alcohols have a C chain length of 10 to 20, and preferably 12 to 18 C atoms. Preferably, mixtures of different C chain lengths such as tallow fatty alcohol or coconut fatty alcohol are used. Examples are Lorol® special ($C_{12-14}$ ROH) or Lorol® technical ($C_{12-18}$ ROH) (both from Cognis). Preferred liquid detergents and cleaning agents comprise 0.01 to 3 wt % and preferably 0.1 to 1 wt % of thickener based on the total amount of agent. In this case, the amount of thickener used depends on the type of thickener and the desired degree of thickening.

Enzymes

The detergents and cleaning agents may comprise enzymes in encapsulated form and/or directly in the detergents and cleaning agents. Particularly suitable enzymes are those from the classes of the hydrolases such as the proteases, esterases, lipases and/or lipolytically acting enzymes, amylases, cellulases and/or other glycosyl hydrolases, hemicellulase, cutinases, β-glucanases, oxidases, peroxidases, perhydrolases and/or lactases and mixtures of the above-mentioned enzymes. All of these hydrolases contribute in laundry to the removal of spots such as protein, fat, or starch-containing spots and greying. Cellulases and other glycosyl hydrolases can also contribute to maintaining the color and softness of the textile by removing pilling and microfibrils. For bleaching or inhibition of color transfer, oxidoreductases can also be used. Particularly suitable are enzymatic agents obtained from bacterial strains or fungi such as *Bacillus subtilis, Bacillus licheniformis, Streptomyces griseus* and *Humicola insolens*. Preferably, proteases of the subtilisin type, and in particular, proteases obtained from *Bacillus lentus* are used. In this context, enzyme mixtures, for example of protease and amylase or protease and lipase and/or lipolytically acting enzymes or protease and cellulase, or of cellulase and lipase and/or lipolytically acting enzymes or protease, lipase and/or lipolytically acting enzymes and cellulase, but in particular, protease and/or lipase-containing mixtures or mixtures with lipolytically acting enzymes, are of particular interest. Examples of such lipolytically acting enzymes are the known cutinases. Peroxidases or oxidases have also been found to be suitable in some cases. The suitable amylases include in particular α-amylases, isoamylases, pullulanases and pectinases. Preferred as cellulases are cellobiohydrolases, endoglucanases and p-glucosidases, also referred to as cellobiases, or mixtures thereof. As various cellulase types differ in their CMCase and avicelase activities, the desired activities can be set by selective mixtures of the cellulases.

The enzymes can be adsorbed onto carriers in order to protect them from premature degradation. For example, the amount of the enzymes, enzyme liquid formulation(s), or enzyme granulates directly contained in detergents and cleaning agents can be approximately 0.01 to 5 wt %, and preferably 0.12 to approximately 2.5 wt %.

However, it may also be preferable, for example in the case of special detergents and cleaning agents for consumers with allergies, for the detergents and cleaning agents not to comprise enzymes.

Electrolytes

Numerous salts of the widest variety may be used as electrolytes from the group of the inorganic salts. Preferred cations are the alkali and alkaline earth metals, and preferred anions are the halides and sulfates. From the standpoint of production technology, the use of NaCl or $MgCl_2$ in the detergents and cleaning agents is preferred. The amount of electrolytes in the detergents and cleaning agents is ordinarily 0.1 to 5 wt %.

Solvents

Non-aqueous solvents that may be used in the liquid detergents and cleaning agents are derived for example from the group of the mono- or polyhydric alcohols, alkanolamines or glycol ethers, provided that they are miscible with water in the given concentration range. Preferably, solvents are selected from ethanol, n- or i-propanol, butanolene, glycol, propane or butane diol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or ethyl ether, diisopropylene glycol monomethyl or ethyl ether, methoxy, ethoxy or butoxy triglycol, 1-butoxyethoxy-2-propanol,3-methyl-3-methoxybutanol, propylene glycol-t-butyl ether and mixtures of these solvents. Non-aqueous solvents may be used in the liquid detergents and cleaning agents in amounts between 0.5 and 15 wt %, but preferably less that 12 wt %, and in particular less than 9 wt %.

Viscosity

The viscosity of the detergents and cleaning agents in liquid form can be measured by the usual standard methods (e.g., using a Brookfield viscometer LVT-II at 20 rpm and 20° C., spindle 3) and for liquid detergents is preferably in the range of 500 to 5000 mPas. Liquid detergents and cleaning agents preferably have viscosities of 700 to 4000 mPas, wherein values of between 1000 and 3000 mPas are particularly preferred. The viscosity of fabric softeners is preferably 20 to 4000 mPas, wherein values between 40 and 2000 mPas are particularly preferred. Particularly preferably, the viscosity of fabric softeners is between 40 and 1000 mPas.

pH-Adjusting Agents

In order to bring the pH of the liquid detergents and cleaning agents into the desired range, the use of pH-adjusting agents may be required. In this case, all known acids or sodium hydroxide solutions are usable, provided that their use is not impossible for applications technology or ecological reasons, or for reasons of consumer protection. The amount of these adjusting agents ordinarily does not exceed 7 wt % based on the formulation as a whole. The pH of liquid detergents and cleaning agents is preferably between 4 and 10, and more preferably between 5.5 and 8.5. The pH of liquid fabric softeners is preferably between 1 and 6, and more preferably between 1.5 and 3.5.

Dyes

In order to improve the esthetic impression of the textile treatment agents, they can be colored using suitable dyes. Preferred dyes that are easy for the person having ordinary skill in the art to select have high storage stability, are insensitive to the other ingredients of the detergents and cleaning agents and to light, and do not show pronounced substantivity with respect to textile fibers so that they will not stain the latter.

Anti-Redeposition Agents

Suitable soil-release polymers, also referred to as "anti-redeposition agents," are for example nonionic cellulose ethers such as methylcellulose and methylhydroxypropyl-cellulose containing 15 to 30 wt % methoxy groups and 1 to 15% hydroxypropyl groups, based in each case on the nonionic cellulose ethers and polymers of phthalic acid and/or terephthalic acid known from the prior art or their derivatives, in particular polymers of ethylene terephthalates and/or polyethylene and/or polypropylene glycol terephthalates or anionic and/or non-ionic modified derivatives thereof. Suitable derivatives include the sulfonated derivatives of phthalic acid and terephthalic acid polymers.

Optical Brighteners

Optical brighteners (so-called "whitening agents") can be added to the detergents and cleaning agents in order to eliminate greying and yellowing of the treated textile surfaces. These substances are absorbed by the fibers, brightening them and simulating a bleaching effect, by converting invisible ultraviolet radiation into visible longer-wavelength light, wherein the ultraviolet light absorbed from sunlight is given off as a slightly blue fluorescence, combining with the yellow color of the greyed or yellowed laundry to give a pure white color. Suitable compounds are derived for example from the substance classes of the 4,4'-diamino-2,2'-stilbene disulfonic acids (flavonic acids), 4,4'-distyryl-biphenylenes, methyl umbelliferones, coumarins, dihydroquinolinones, 1,3-diarylpyrazolines, naphthalic acid imides, benzoxazole, benzisoxazole and benzimidazole systems, and heterocycle-substituted pyrene derivatives. The optical brighteners are ordinarily used in amounts of between 0% and 0.3 wt %, relative to the finished detergents and cleaning agents.

Greying Inhibitors

The purpose of greying inhibitors is to keep the dirt detached from the fibers suspended in the liquor, thus preventing the dirt from being reabsorbed. Water-soluble colloids, mostly of the organic type, are suitable for this purpose, such as glue, gelatin, salts of ether sulfonic acids of starch or cellulose or salts of acidic sulfuric acid esters of cellulose or starch. Water-soluble polyamides comprising acid groups are also suitable for this purpose. Moreover, soluble starch preparations and starch products other than those mentioned above can also be used, for example degraded, aldehyde starches, etc. Polyvinylpyrrolidone can also be used. However, cellulose ethers such as carboxymethyl cellulose (Na salt), methyl cellulose, hydroxyalkyl cellulose and mixed ethers such as methyl hydroxyethyl cellulose, methyl hydroxypropyl cellulose, methyl carboxymethyl cellulose, and mixtures thereof in amounts of 0.1 to 5 wt %, based on the detergents and cleaning agents, should preferably be used.

Anti-Creasing Agents

As textile fabrics, composed in particular of rayon, cellulose, cotton and mixtures thereof, can tend to form creases because the individual fibers are sensitive to flexing, bending, pressing, and crushing across the fiber direction, the detergents and cleaning agents can comprise anti-creasing agents. These include for example synthetic products based on fatty acids, fatty acid esters, fatty acid amides, -alkylol esters, -alkylolamides or fatty alcohols, which are usually reacted with ethylene oxide, or products based on lecithin or modified phosphoric acid esters.

Antimicrobial Agents

The detergents and cleaning agents can comprise antimicrobial agents in order to combat microorganisms. In this case, a distinction is made depending on the antimicrobial spectrum and mechanism of action between bacteriostats and bactericides, fungistats and fungicides, etc. Examples of important substances from these groups are benzalkonium chlorides, alkylaryl sulfonates, halophenols and phenylmercuric acetates, wherein these compounds may also be dispensed with entirely in the detergents and cleaning agents according to the invention.

Preservatives

The detergents and cleaning agents according to the invention can comprise preservatives, wherein preferably only preservatives are used that have no or only minor potential to sensitize the skin. Examples are sorbic acid and salts thereof, benzoic acid and salts thereof, salicylic acid and salts thereof, phenoxyethanol, 3-iodo-2-propynyl butylcarbamate, sodium N-(hydroxymethyl)glycinate, biphenyl-2-ol and mixtures thereof. A suitable preservative is the solvent-free, aqueous combination of diazolidinyl urea, sodium benzoate and potassium sorbate (obtainable as Euxyl® K 500 from Schülke and Mayr), which may be used in a pH range of up to 7. Preservatives based on organic acids and/or salts thereof are particularly suitable for preserving the skin-friendly detergents and cleaning agents according to the invention.

Antioxidants

In order to prevent undesired changes in the detergents and cleaning agents and/or the treated textile surfaces caused by the action of oxygen and other oxidative processes, the detergents and cleaning agents can comprise antioxidants. Examples of compounds of this class include substituted phenols, hydroquinones, pyrocatechols and aromatic amines, and organic sulfides, polysulfides, dithiocarbamates, phosphites, phosphonates and vitamin E.

Antistatics

Increased wearing comfort can be achieved by the additional use of antistatics in the detergents and cleaning agents. Antistatics increase the surface conductivity, thus allowing built-up charges to be more easily discharged. As a rule, antistatics are substances with at least one hydrophilic molecular ligand that provide a more or less hygroscopic film on surfaces. These antistatics, which are usually surface-active, can be divided into nitrogen-containing (amines, amides, quaternary ammonium compounds), phosphorus-containing (phosphoric acid esters) and sulfur-containing (alkyl sulfonates, alkyl sulfates) antistatics. Lauryl-(or stearyl)dimethylbenzyl ammonium chlorides are suitable as antistatics for textile surfaces or as additives to detergents and cleaning agents, wherein an additional conditioning effect is also achieved.

Foam Inhibitors

Silicone derivatives, for example, may be used in textile treatment agents in order to improve rewettability and facilitate ironing of treated textile surfaces. These further improve the rinsing behavior of the detergents and cleaning agents by means of their foam-inhibiting properties. Preferred silicone derivatives are for example polydialkyl or alkylaryl siloxanes in which the alkyl groups have one to five C atoms and are completely or partially fluorinated. Preferred silicones are polydimethylsiloxanes, which can optionally be derivatized and are then aminofunctional or quaternized or have Si—OH, Si—H and/or Si—Cl bonds. The viscosities of the preferred silicones at 25° C. are in the range of 100 to 100,000 mPas, wherein the silicones may be used in amounts of between 0.2 and 5 wt % based on the detergents and cleaning agents as a whole.

UV Absorbers

Finally, the detergents and cleaning agents can also comprise UV absorbers that are absorbed onto the treated textile surface and improve the light stability of the fibers. Examples of compounds having these desired properties are the compounds and derivatives of benzophenone with substituents in the 2 and/or 4 position that act by non-radiative deactivation. Also suitable are substituted benzotriazoles, acrylates substituted at the 3 position (cinnamic acid derivatives), optionally with cyano groups in the 2 position, salicylates, organic Ni complexes and natural substances such as umbelliferone and endogenous urocanic acid.

Heavy Metal Complexing Agents

In order to prevent the decomposition of certain detergent ingredients catalyzed by heavy metals, substances that complex heavy metals may be used. Suitable heavy metal complexing agents are for example the alkali salts of ethylene diamine tetra-acetic acid (EDTA) or nitrilotriacetic acid (NTA) and alkali metal salts of anionic polyelectrolytes such as polymaleates and polysulfonates. A preferred class of complexing agents are the phosphonates, which are included in preferred textile treatment agents in amounts of 0.01 to 2.5 wt %, preferably 0.02 to 2 wt % and in particular 0.03 to 1.5 wt %. Examples of these preferred compounds include in particular organophosphonates such as e.g. 1-hydroxyethane-1,1-diphosphonic acid (HEDP), aminotri(methylene phosphonic acid) (ATMP), diethylene triamine penta(methylene phosphonic acid) (DTPMP or DETPMP) and 2-phosphonobutane-1,2,4-tricarboxylic acid (PBS-AM), which are usually used in the form of their ammonium or alkali metal salts.

Production of the Preparations

The production of liquid detergents and cleaning agents can be carried out by means of common and known methods and processes, for example by simply mixing the components in stirred vessels, wherein water, non-aqueous solvents and surfactants are preferably first placed in the vessels, after which the further components are added in portions. In this manner, liquid detergents and cleaning agents can be produced by first adding the acidic components such as e.g. the linear alkyl sulfonates, citric acid, boric acid, phosphonic acid, fatty alcohol ether sulfates, etc. and the nonionic surfactants. The solvent component is preferably also added at this time, but this addition can also be carried out later. The thickener, for example a polyacrylate, can be added to these components. A base such as e.g. NaOH, KOH, triethanolamine or monoethanolamine, followed by the fatty acid if present, is then added. After this, the remaining ingredients and the remaining solvents of the aqueous liquid detergents and cleaning agents are added to the mixture, and the pH is set to approximately 8.5. Finally, the particles to be dispersed can be added and mixed to homogeneously disperse them in the aqueous liquid detergents and cleaning agents.

Use

A last subject matter of the invention relates to use of a fragrance composition comprising at least one fragrance that has an aldehyde or acetal functional group and an acid number of at most 5 mg KOH/g, and in particular at most 3 mg KOH/g, for producing fragrance capsules.

EXAMPLES

General Manufacturing Instructions

A total of 20 different fragrance compositions with differing acid numbers were encapsulated according to a standard method, and their stability in a fabric softener formulation at 40° C. was then investigated. The composition of the capsules is shown in Table 1 below:

TABLE 1

Composition of fragrance capsules

| Phase | Component | amounts [g] |
|---|---|---|
| External phase | Water | 243.0 |
|  | Polyvinyl alcohol Celvol 523 | 2.5 |
| Internal phase | Fragrance mixture | 184.0 |
|  | Polyisocyanate (Fennosize SOXA WM33 | 20.5 |
| Crosslinking phase | Crosslinker (guanidine carbonate) | 6.1 |
|  | Water | 40.5 |

The acid number of the internal phase was determined immediately prior to encapsulation according to DIN EN ISO 660:2009-10. The capsules were produced by the following series of steps:
1. provision of the external phase;
2. provision of the internal phase;
3. optional heating of the two phases until clear;

4. mixing of the internal and external phases;
5. emulsification of the mixture using high shearing force (850 rpm);
6. addition of the crosslinker;
7. heating of the mixture from 40 to 80° C. over a period of 5 h;
8. stirring of the mixture for a further 4 h at 80° C., followed by cooling.

The capsules obtained in this manner showed a D50 value of approx. 24 μm and a D90 value of approx. 44 μm.

The stability of the produced capsules was determined by incorporating the capsules into a fabric softener formulation (approx. 15% esterquat) in a concentration of 1% and then storing this mixture at 40° C. After this, the concentration of the fragrances diffused into the fabric softener formulation was determined by means of GC headspace measurements. These results were then used to calculate the residual content of perfume oil remaining in the capsules.

FIG. 1 shows the stability of the capsules depending on the acid number of the fragrance mixture. It can be seen immediately that capsules containing fragrance preparations with acid numbers greater than 5 mg KOH/g no longer show sufficient diffusion stability in the application formulation, with more than 90% of the capsule content bleeding out into the application formulation. If the acid number is less than 5 mg KOH/g, and in particular less than 3 mg KOH/g, the capsules are sufficiently stable, so that at least 50% of the contents remain in the capsules after 4 weeks of storage.

The invention claimed is:

1. A method for producing fragrance capsules with improved surfactant stability, comprising the following steps:
   (a) providing a fragrance composition comprising at least one fragrance which has at least one functional group capable by oxidation or hydrolysis of forming an acid group;
   (b) determining amount of free carboxylic acids in said composition; and
   (c) encapsulating the fragrance composition when said fragrance composition has an acid number immediately prior to encapsulation of at most 5 mg KOH/g.

2. The method as claimed in claim 1, wherein a fragrance composition is used that has an acid number immediately prior to encapsulation of at most 3 mg KOH/g.

3. The method as claimed in claim 1, wherein a fragrance composition is used that comprises at least one fragrance having an aldehyde, acetal, ester or lactone functional group.

4. The method as claimed in claim 1, wherein a fragrance composition is used that comprises at least one fragrance selected from the group consisting of
   (i) aliphatic aldehydes and their acetals,
   (ii) cycloaliphatic aldehydes,
   (iii) aromatic or araliphatic aldehydes,
   (iv) aliphatic, aromatic or araliphatic esters,
   (v) lactones, and mixtures thereof.

5. The method as claimed in claim 3, wherein aldehydes or their acetals are used that are selected from the group consisting of hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyloxyacetaldehyde, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde, benzaldehyde; phenylacetaldehyde; 3-phenylpropanal; hydratropic aldehyde; 4-methylbenzaldehyde; 4-methylphenyl-acetaldehyde; 3-(4-ethylphenyl)-2,2-dimethylpropanal; 2-methyl-3-(4-isopropyl-phenyl)propanal; 2-methyl-3-(4-tert-butylphenyl)propanal; 3-(4-tert-butylphenyl)propanal; cinnamaldehyde; α-butylcinnamaldehyde; α-amylcinnamaldehyde; α-hexylcinnamaldehyde; 3-methyl-5-phenylpentanal; 4-m ethoxybenzaldehyde; 4-hydroxy-3-m ethoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal and mixtures thereof.

6. The method as claimed in claim 3, wherein esters or lactones are used that are selected from the group consisting of E)- and (Z)-3-hexenyl formiate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate; B. 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate; benzyl acetate; benzyl propionate; benzyl isobutyrate; benzyl isovalerate; 2-phenethyl acetate; 2-phenethyl propionate; 2-phenethyl isobutyrate; 2-phenethyl isovalerate; 1-phenethyl acetate; α-trichlormethylbenzyl acetate; α,α-dimethylphenethyl acetate; α,α-dimethylphenethyl butyrate; cinnamyl acetate; 2-phenoxyethyl isobutyrate; 4-methoxybenzyl acetate; allyl-3-cyclohexyl propionate; allylcyclohexyl oxyacetate; methyl dihydrojasmonate; methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate; methyl benzoate; ethyl benzoate; hexyl benzoate; benzyl benzoate; methylphenyl acetate; ethyl phenyl acetate; geranyl phenyl acetate; phenethyl phenylacetate; methyl cinnamate; ethyl cinnamate; benzyl cinnamate; phenethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenethyl salicylate; methyl-2,4-dihydroxy-3,6-dimethyl benzoate; ethyl-3-phenylglycidate; ethyl-3-methyl-3-phenylglycidate and mixtures thereof.

7. The method as claimed in claim 1, wherein a fragrance composition is used that comprises at least one further fragrance that has neither an aldehyde nor an acetal, ester or lactone functional group.

8. Fragrance capsules, comprising said fragrance composition having an acid number immediately prior to encapsulation of less than 5 mg KOH/g and obtained by the method as claimed in claim 1.

9. The capsules as claimed in claim 8, present as macrocapsules with diameters of approximately 0.1 to approximately 5 mm or microcapsules with diameters of approximately 0.0001 to approximately 0.1 mm.

10. The capsules as claimed in claim 8, wherein the capsule shell is composed of substances that are selected from the group consisting of dextrins, maltodextrins, gelatins, gum arabic, agar-agar, ghatti gum, gellan gum, modified and unmodified celluloses, pullulan, curdlan, carrageenans, alginic acid, alginate, pectin, inulin, xanthan gum, alginic acid, alginates, chitosan, synthetic, anionic or cationic polymers, reaction products of two or more of these substances and mixtures thereof.

11. An agent comprising the fragrance capsules as claimed in claim 8.

12. The agent as claimed in claim 11, which is a cosmetic agent.

13. The agent as claimed in claim 11, which is a detergent, rinsing agent, or cleaning agent.

14. The agent as claimed in claim 11, comprising the fragrance capsules in amounts of approximately 0.01 to approximately 10 wt % based on the agent.

15. A fragrance composition comprising at least one fragrance that has an aldehyde or acetal functional group and acid number of at most 5 mg KOH/g, for producing fragrance capsules by the method as claimed in claim 1.

16. An agent comprising the fragrance capsules obtained by the method as claimed in claim 1.

17. The agent as claimed in claim 16, which is a cosmetic agent.

18. The agent as claimed in claim 16, which is a detergent, rinsing agent, or cleaning agent.

19. The agent as claimed in claim 16, comprising the fragrance capsules in amounts of approximately 0.01 to approximately 10 wt % based on the agent.

* * * * *